US009856323B2

(12) United States Patent
Short et al.

(10) Patent No.: US 9,856,323 B2
(45) Date of Patent: Jan. 2, 2018

(54) ANTI-CD22 ANTIBODIES

(71) Applicant: BIOATLA, LLC, San Diego, CA (US)

(72) Inventors: Jay Short, Del Mar, CA (US);
Gerhard Frey, San Diego, CA (US);
Hwai Wen Chang, San Marcos, CA (US); William Boyle, Malibu, CA (US)

(73) Assignee: BIOATLA, LLC, San Diego, CA (US)

(*) Notice: Subject to any disclaimer, the term of this patent is extended or adjusted under 35 U.S.C. 154(b) by 294 days.

(21) Appl. No.: 14/396,869

(22) PCT Filed: Apr. 26, 2013

(86) PCT No.: PCT/US2013/038370
§ 371 (c)(1),
(2) Date: Oct. 24, 2014

(87) PCT Pub. No.: WO2013/163519
PCT Pub. Date: Oct. 31, 2013

(65) Prior Publication Data
US 2015/0086562 A1    Mar. 26, 2015

Related U.S. Application Data

(60) Provisional application No. 61/638,834, filed on Apr. 26, 2012.

(51) Int. Cl.
*A61K 39/395* (2006.01)
*C07K 16/28* (2006.01)
*C07K 16/30* (2006.01)
*A01K 67/027* (2006.01)
*A61K 39/00* (2006.01)

(52) U.S. Cl.
CPC ...... *C07K 16/3061* (2013.01); *A01K 67/0275* (2013.01); *C07K 16/2803* (2013.01); *C07K 16/2851* (2013.01); *A01K 2267/01* (2013.01); *A61K 2039/505* (2013.01); *C07K 2317/33* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,789,554 A | 8/1998 | Leung et al. | |
| 2004/0110226 A1* | 6/2004 | Lazar | C07K 16/00 435/7.1 |
| 2008/0050310 A1 | 2/2008 | Ebens, Jr. et al. | |

FOREIGN PATENT DOCUMENTS

| | | |
|---|---|---|
| JP | 10505231 A | 5/1998 |
| JP | 2006506955 A | 3/2006 |
| JP | 2010511388 A | 4/2010 |
| WO | WO9604925 A1 | 2/1996 |
| WO | WO03093320 A2 | 11/2003 |
| WO | WO2007103469 A2 | 9/2007 |
| WO | WO2008070569 A2 | 6/2008 |
| WO | WO2014057118 A1 | 4/2014 |

OTHER PUBLICATIONS

Rudikoff et al., Proc Natl Acad Sci USA 79: 1979-1983 (1982).*
Colman,. Research in Immunology 145: 33-36 (1994).*
Kussie et al., J. Immunol. 152: 146-152 (1994).*
Chen et al., EMBO J., 14: 2784-2794 (1995).*
Steinfeld et al. (Expert Opin. Biol. Ther. 6: 943-949, 2006).*
Levesque et al., J Allergy CLin Immunol 121: 13-21 (2008).*
Newton et al., Expert Opin. Biol. Ther. 1: 995-1003 (2001).*
Arndt, M., et al., "Generation of a Highly Stable, Internalizing Anti-CD22 Single-Chain Fv Fragment for Targeting Non-Hodgkin's Lymphoma," Int. J. Cancer, Dec. 10, 2003, vol. 107, No. 5, pp. 822-829.
International Preliminary Report on Patentability; dated Oct. 28, 2014 for corresponding PCT Application No. PCT/US2003/038370.
European Search Report; dated Mar. 16, 2016 for EP Application No. EP13781426.5.
Leung, Shui-on, et al. "Construction and characterization of a humanized, internalizing, B-cell (CD22)-specific, leukemia/lymphoma antibody, LL2." Molecular immunology 32.17 (1995): 1413-1427.
Carnahan, Josette, et al. "Epratuzumab, a CD22-targeting recombinant humanized antibody with a different mode of action from rituximab." Molecular immunology 44.6 (2007): 1331-1341.
Chinese Office Action; dated Jul. 6, 2016 for CN Application No. CN201380022320.0.
Deyev, S. M., and E. N. Lebedenko. "Modern technologies for creating synthetic antibodies for clinical application." Acta Naturae англоязычная версия 1.1 (1) (2009), pp. 32-50.
Russian Office Action; dated Feb. 17, 2017 for RU Application No. RU 2014147452.
Australian Examination Report; dated May 4, 2017 for AU Application No. AU 2013251482.
Japanese Notice of Refusal; dated Jan. 31, 2017 for JP Application No. JP2015-509172.
Chinese Office Action; dated Mar. 29, 2017 for CN Application No. CN 2013/0022320.0.
Russian Office Action; dated Jun. 15, 2017 for RU Application No. RU2014147452.
Rudikoff, Stuart, et al. "Single amino acid substitution altering antigen-binding specificity." Proceedings of the National Academy of Sciences 79.6 (1982): 1979-1983.

(Continued)

*Primary Examiner* — Phillip Gambel
(74) *Attorney, Agent, or Firm* — Mendelsohn Dunleavy, P.C.

(57) ABSTRACT

Anti-CD22 antibodies, including isolated nucleic acids that encode at least one such anti-CD22 antibody, vectors, host cells, transgenic animals or plants, and methods of making and using thereof, including therapeutic compositions, methods and devices.

22 Claims, 25 Drawing Sheets

(56) References Cited

OTHER PUBLICATIONS

Ohno, S., et al. "Antigen-binding specificities of antibodies are primarily determined by seven residues of VH." Proceedings of the National Academy of Sciences 82.9 (1985): 2945-2949.
Japanese Office Action; dated Oct. 31, 2017 for Japanese Application No. JP2015-509172.

* cited by examiner

SEQ ID NO:1
VM1000 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAGGGGGGTCCCAT
CAAGGTTCAGTGGAAGTGGATCTGGGACAGATTTTACTTTCACCATCAGCAGCCTGCAGCCTGAA
GATATTGCAACATATTACTGTAAGCAATACCTCTCCTCGTGGACGTTCGGCCAAGGG

SEQ ID NO:17
VM1000 LC
EIVLTQSPATLSLSPGERATLSCKSSQSVLYSAVEKNYLAWYQQKPGKAPKLLIYWASTRERGVPSRFS
GSGSGTDFTFTISSLQPEDIATYYCKQYLSSWTFGQG

SEQ ID NO:33
VM1000 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGACTCACCATCTCCAAGGACACCTCCAAAAACCAGGTGGTCCTTACAATGACCAACATGGACC
CTGTGGACACAGCCACGTATTACTGTGCAAGAAGGGGGATTACTACGTTCTACTGGGGCCAGGGA

SEQ ID NO:49
VM1000 HC
QVQLVQSGAEVKKPGASVKVSCKASGYVFTSYWLHWIRQSPSRGLEWLGYINPRNDYTEYNRIFKGR
LTISKDTSKNQVVLTMTNMDPVDTATYYCARRGITTFYWGQG

FIGURE 1

SEQ ID NO:2
VM1001 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:18
VM1001 LC
EIVLTQSPATLSLSPGERATLSCKSSQSVLYSAVEKNYLAWYQQKPGQAPRLLIYWASTRERGIPDRFS
GSGSGTDFTLTISRLEPEDFAVYYCKQYLSSWTFGQG

SEQ ID NO:34
VM1001 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGACTCACCATCTCCAAGGACACCTCCAAAAACCAGGTGGTCCTTACAATGACCAACATGGACC
CTGTGGACACAGCCACGTATTACTGTGCAAGAAGGGGGATTACTACGTTCTACTGGGGCCAGGGA

SEQ ID NO:50
VM1001 HC
QVQLVQSGAEVKKPGASVKVSCKASGYVFTSYWLHWIRQSPSRGLEWLGYINPRNDYTEYNRIFKGR
LTISKDTSKNQVVLTMTNMDPVDTATYYCARRGITTFYWGQG

FIGURE 2

SEQ ID NO:3
VM1002 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:19
VM1002 LC
EIVLTQSPATLSLSPGERATLSCKSSQSVLYSAVEKNYLAWYQQKPGQAPRLLIYWASTRERGIPDRFS
GSGSGTDFTLTISRLEPEDFAVYYCKQYLSSWTFGQG

SEQ ID NO:35
VM1002 HC
GAAGTGCAGCTGGTGCAGTCTGGAGCAGAGGTGAAAAAGCCCGGGGAGTCTCTGAGGATCTCCTG
TAAGGGTTCTGGCTACGTTTTTACTAGCTACTGGCTGCACTGGGTGCGACAGGCCCCTGGACAAGG
GCTTGAGTGGATGGGTTACATTAATCCTAGGAATGATTATACTGAGTACAATCGGATTTTCAAGGG
GAGAGTCACGATTACCGCGGACAAATCCACGAGCACAGCCTACATGGAGCTGAGCAGCCTGAGAT
CTGAGGACACGGCCGTGTATTACTGTGCGAGAAGGGGGATTACTACGTTCTACTGGGGCCAGGGA

SEQ ID NO:51
VM1002 HC
EVQLVQSGAEVKKPGESLRISCKGSGYVFTSYWLHWVRQAPGQGLEWMGYINPRNDYTEYNRIFKGR
VTITADKSTSTAYMELSSLRSEDTAVYYCARRGITTFYWGQG

FIGURE 3

SEQ ID NO:4
VM1003 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:20
VM1003 LC
EIVLTQSPATLSLSPGERATLSCKSSQSVLYSAVEKNYLAWYQQKPGQAPRLLIYWASTRERGIPDRFS
GSGSGTDFTLTISRLEPEDFAVYYCKQYLSSWTFGQG

SEQ ID NO:36
VM1003 HC
GAGGTCCAGCTGGTACAGTCTGGGGCTGAGGTGAAGAAGCCTGGGGCTACAGTGAAAATCTCCTG
CAAGGTTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTTGTCTTCTCCTTGGACACCTCTGTCAGCACGGCATATCTGCAGATCTGCAGCCTAAAGGC
TGAGGACACTGCCGTGTATTACTGTGCGAGAAGGGGGATTACTACGTTCTACTGGGGCCAGGGA

SEQ ID NO:52
VM1003 HC
EVQLVQSGAEVKKPGATVKISCKVSGYVFTSYWLHWIRQSPSRGLEWLGYINPRNDYTEYNRIFKGRF
VFSLDTSVSTAYLQICSLKAEDTAVYYCARRGITTFYWGQG

FIGURE 4

SEQ ID NO:5
VM1004 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:21
VM1004 LC
EIVLTQSPATLSLSPGERATLSCKSSQSVLYSAVEKNYLAWYQQKPGKAPKLLIYWASTRERGIPDRFS
GSGSGTDFTLTISRLEPEDFAVYYCKQYLSSWTFGQG

SEQ ID NO:37
VM1004 HC
GAGGTCCAGCTGGTACAGTCTGGGGCTGAGGTGAAGAAGCCTGGGGCTACAGTGAAAATCTCCTG
CAAGGTTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTTGTCTTCTCCTTGGACACCTCTGTCAGCACGGCATATCTGCAGATCTGCAGCCTAAAGGC
TGAGGACACTGCCGTGTATTACTGTGCGAGAAGGGGGATTACTACGTTCTACTGGGGCCAGGGA

SEQ ID NO:53
VM1004 HC
EVQLVQSGAEVKKPGATVKISCKVSGYVFTSYWLHWIRQSPSRGLEWLGYINPRNDYTEYNRIFKGRF
VFSLDTSVSTAYLQICSLKAEDTAVYYCARRGITTFYWGQG

FIGURE 5

SEQ ID NO:6
VM1005 LC
GCCATCCAGTTGACCCAGTCTCCATCCTCCCTGTCTGCATCTGTAGGAGACAGAGTCACCATCACT
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGGTCCCAT
CAAGGTTCAGCGGCAGTGGATCTGGGACAGATTTCACTCTCACCATCAGCAGCCTGCAGCCTGAA
GATTTTGCAACTTATTACTGTAAGCAATACCTCTCCTCGTGGACGTTCGGCCAAGGG

SEQ ID NO:22
VM1005 LC
AIQLTQSPSSLSASVGDRVTITCKSSQSVLYSAVEKNYLAWYQQKPGQAPRLLIYWASTRERGVPSRFS
GSGSGTDFTLTISSLQPEDFATYYCKQYLSSWTFGQG

SEQ ID NO:38
VM1005 HC
GAGGTCCAGCTGGTACAGTCTGGGGCTGAGGTGAAGAAGCCTGGGGCTACAGTGAAAATCTCCTG
CAAGGTTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTTGTCTTCTCCTTGGACACCTCTGTCAGCACGGCATATCTGCAGATCTGCAGCCTAAAGGC
TGAGGACACTGCCGTGTATTACTGTGCGAGAAGGGGGATTACTACGTTCTACTGGGGCCAGGGA

SEQ ID NO:54
VM1005 HC
EVQLVQSGAEVKKPGATVKISCKVSGYVFTSYWLHWIRQSPSRGLEWLGYINPRNDYTEYNRIFKGRF
VFSLDTSVSTAYLQICSLKAEDTAVYYCARRGITTFYWGQG

FIGURE 6

SEQ ID NO:7
VM1006 LC
GACATCCAGATGACCCAGTCTCCATCCTCCCTGTCTGCATCTGTAGGAGACAGAGTCACCATCACT
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:23
VM1006 LC
DIQMTQSPSSLSASVGDRVTITCKSSQSVLYSAVEKNYLAWYQQKPGKAPKLLIYWASTRERGIPDRFS
GSGSGTDFTLTISRLEPEDFAVYYCKQYLSSWTFGQG

SEQ ID NO:39
VM1006 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTTGTCTTCTCCTTGGACACCTCTGTCAGCACGGCATATCTGCAGATCTGCAGCCTAAAGGC
TGAGGACACTGCCGTGTATTACTGTGCGAGAAGGGGGATTACTACGTTCTACTGGGGCCAGGGA

SEQ ID NO:55
VM1006 HC
QVQLVQSGAEVKKPGASVKVSCKASGYVFTSYWLHWIRQSPSRGLEWLGYINPRNDYTEYNRIFKGR
FVFSLDTSVSTAYLQICSLKAEDTAVYYCARRGITTFYWGQG

FIGURE 7

SEQ ID NO:8
VM1007 LC
GCCATCCAGTTGACCCAGTCTCCATCCTCCCTGTCTGCATCTGTAGGAGACAGAGTCACCATCACT
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAAGGGGGGTCCCCT
CGAGGTTCAGTGGCAGTGGATCTGGGACAGATTTCACCTTTACCATCAGTAGCCTGGAAGCTGAA
GATGCTGCAACATATTACTGTAAGCAATACCTCTCCTCGTGGACGTTCGGCCAAGGG

SEQ ID NO:24
VM1007 LC
AIQLTQSPSSLSASVGDRVTITCKSSQSVLYSAVEKNYLAWYQQKPGKAPKLLIYWASTRERGVPSRFS
GSGSGTDFTFTISSLEAEDAATYYCKQYLSSWTFGQG

SEQ ID NO:40
VM1007 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGGTGCGACAGGCTCGTGGACAACG
CCTTGAGTGGATAGGTTACATTAATCCTAGGAATGATTATACTGAGTACAATCGGATTTTCAAGGG
GAGAGTCACGATTACCGCGGACAAATCCACGAGCACAGCCTACATGGAGCTGAGCAGCCTGAGAT
CTGAGGACACGGCCGTGTATTACTGTGCGAGAAGGGGGATTACTACGTTCTACTGGGGCCAGGGA

SEQ ID NO:56
VM1007 HC
QVQLVQSGAEVKKPGASVKVSCKASGYVFTSYWLHWVRQARGQRLEWIGYINPRNDYTEYNRIFKG
RVTITADKSTSTAYMELSSLRSEDTAVYYCARRGITTFYWGQG

FIGURE 8

SEQ ID NO:9
VM1008 LC
GACATCCAGATGACCCAGTCTCCATCCTCCCTGTCTGCATCTGTAGGAGACAGAGTCACCATCACT
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:25
VM1008 LC
DIQMTQSPSSLSASVGDRVTITCKSSQSVLYSAVEKNYLAWYQQKPGQAPRLLIYWASTRERGIPDRFS
GSGSGTDFTLTISRLEPEDFAVYYCKQYLSSWTFGQG

SEQ ID NO:41
VM1008 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGGTGCGACAGGCTCGTGGACAACG
CCTTGAGTGGATAGGTTACATTAATCCTAGGAATGATTATACTGAGTACAATCGGATTTTCAAGGG
GAGAGTCACGATTACCGCGGACAAATCCACGAGCACAGCCTACATGGAGCTGAGCAGCCTGAGAT
CTGAGGACACGGCCGTGTATTACTGTGCGAGAAGGGGGATTACTACGTTCTACTGGGGCCAGGGA

SEQ ID NO:57
VM1008 HC
QVQLVQSGAEVKKPGASVKVSCKASGYVFTSYWLHWVRQARGQRLEWIGYINPRNDYTEYNRIFKG
RVTITADKSTSTAYMELSSLRSEDTAVYYCARRGITTFYWGQG

SEQ ID NO:10
VM1009 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAAGGGGGGTCCCCT
CGAGGTTCAGTGGCAGTGGATCTGGGACAGATTTCACCTTTACCATCAGTAGCCTGGAAGCTGAA
GATGCTGCAACATATTACTGTAAGCAATACCTCTCCTCGTGGACGTTCGGCCAAGGG

SEQ ID NO:26
VM1009 LC
EIVLTQSPATLSLSPGERATLSCKSSQSVLYSAVEKNYLAWYQQKPGKAPKLLIYWASTRERGVPSRFS
GSGSGTDFTFTISSLEAEDAATYYCKQYLSSWTFGQG

SEQ ID NO:42
VM1009 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTTGTCTTCTCCTTGGACACCTCTGTCAGCACGGCATATCTGCAGATCTGCAGCCTAAAGGC
TGAGGACACTGCCGTGTATTACTGTGCGAGAAGGGGGATTACTACGTTCTACTGGGGCCAGGGA

SEQ ID NO:58
VM1009 HC
QVQLVQSGAEVKKPGASVKVSCKASGYVFTSYWLHWIRQSPSRGLEWLGYINPRNDYTEYNRIFKGR
FVFSLDTSVSTAYLQICSLKAEDTAVYYCARRGITTFYWGQG

FIGURE 10

SEQ ID NO:11
VM1010 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTATCAGCA
GAAACCAGGGAAAGCTCCTAAGCTCCTGATCTATTGGGCATCCACTAGGGAAAGGGGGGTCCCAT
CAAGGTTCAGTGGAAGTGGATCTGGGACAGATTTTACTTTCACCATCAGCAGCCTGCAGCCTGAA
GATATTGCAACATATTACTGTAAGCAATACCTCTCCTCGTGGACGTTCGGCCAAGGG

SEQ ID NO:27
VM1010 LC
EIVLTQSPATLSLSPGERATLSCKSSQSVLYSAVEKNYLAWYQQKPGKAPKLLIYWASTRERGVPSRFS
GSGSGTDFTFTISSLQPEDIATYYCKQYLSSWTFGQG

SEQ ID NO:43
VM1010 HC
GAAGTGCAGCTGGTGCAGTCTGGAGCAGAGGTGAAAAAGCCCGGGGAGTCTCTGAGGATCTCCTG
TAAGGTTTCTGGCTACGTTTTTACTAGCTACTGGCTGCACTGGATCAGGCAGTCCCCATCGAGAGG
CCTTGAGTGGCTGGGTTACATTAATCCTAGGAATGATTATACTGAGTACAATCGGATTTTCAAGGG
GAGATTCACCATCTCCAGAGACAACGCCAAGAACTCACTGTATCTGCAAATGAACAGCCTGAGAG
CCGAGGACACGGCTGTGTATTACTGTGCGAGAAGGGGGATTACTACGTTCTACTGGGGCCAGGGA

SEQ ID NO:59
VM1010 HC
EVQLVQSGAEVKKPGESLRISCKVSGYVFTSYWLHWIRQSPSRGLEWLGYINPRNDYTEYNRIFKGRFT
ISRDNAKNSLYLQMNSLRAEDTAVYYCARRGITTFYWGQG

FIGURE 11

SEQ ID NO:12
VM1011 LC
GAAATTGTGTTGACACAGTCTCCAGCCACCCTGTCTTTGTCTCCAGGGGAAAGAGCCACCCTCTCC
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGATCCCAG
ACAGGTTCAGTGGCAGTGGGTCTGGGACAGACTTCACTCTCACCATCAGCAGACTGGAGCCTGAA
GATTTTGCAGTGTATTACTGTAAGCAATACCTCTCCTCGTGGACGTTCGGCCAAGGG

SEQ ID NO:28
VM1011 LC
EIVLTQSPATLSLSPGERATLSCKSSQSVLYSAVEKNYLAWYQQKPGQAPRLLIYWASTRERGIPDRFS
GSGSGTDFTLTISRLEPEDFAVYYCKQYLSSWTFGQG

SEQ ID NO:44
VM1011 HC
CAGGTGCAGCTGCAGGAGTCGGGCCCAGGACTGGTGAAGCCTTCACAGACCCTGTCCCTCACCTG
CACTGTCTCTGGCTACGTTTTTACTAGCTACTGGCTGCACTGGATCCGCCAGCCCCCAGGGAAGGG
GCTGGAGTGGATTGGTTACATTAATCCTAGGAATGATTATACTGAGTACAATCGGATTTTCAAGGG
GAGAGTCACGATTACCGCGGACAAATCCACGAGCACAGCCTACATGGAGCTGAGCAGCCTGAGAT
CTGAGGACACGGCCGTGTATTACTGTGCGAGAAGGGGGATTACTACGTTCTACTGGGGCCAGGGA

SEQ ID NO:60
VM1011 HC
QVQLQESGPGLVKPSQTLSLTCTVSGYVFTSYWLHWIRQPPGKGLEWIGYINPRNDYTEYNRIFKGRVT
ITADKSTSTAYMELSSLRSEDTAVYYCARRGITTFYWGQG

FIGURE 12

SEQ ID NO:13
VM1012 LC
GAAATTGTGTTGACACAGTCTCCAGCCACCCTGTCTGTGTCTCCAGGGGAAAGAGCCACCCTCTCC
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGGTCCCAT
CAAGGTTCAGTGGAAGTGGATCTGGGACAGATTTTACTTTCACCATCAGCAGCCTGCAGCCTGAA
GATATTGCAACATATTACTGTAAGCAATACCTCTCCTCGTGGACGTTCGGCCAAGGG

SEQ ID NO:29
VM1012 LC
EIVLTQSPATLSVSPGERATLSCKSSQSVLYSAVEKNYLAWYQQKPGQAPRLLIYWASTRERGVPSRFS
GSGSGTDFTFTISSLQPEDIATYYCKQYLSSWTFGQG

SEQ ID NO:45
VM1012 HC
CAGGTTCAGCTGGTGCAGTCTGGAGCTGAGGTGAAGAAGCCTGGGGCCTCAGTGAAGGTCTCCTG
CAAGGCTTCTGGCTACGTTTTTACTAGCTACTGGCTGCACTGGGTGCGACAGGCCCCTGGACAAGG
GCTTGAGTGGATGGGTTACATTAATCCTAGGAATGATTATACTGAGTACAATCGGATTTTCAAGGG
GAGATTCACCATCTCCAGAGACAACGCCAAGAACTCACTGTATCTGCAAATGAACAGCCTGAGAG
CCGAGGACACGGCTGTGTATTACTGTGCGAGAAGGGGGATTACTACGTTCTACTGGGGCCAGGGA

SEQ ID NO:61
VM1012 HC
QVQLVQSGAEVKKPGASVKVSCKASGYVFTSYWLHWVRQAPGQGLEWMGYINPRNDYTEYNRIFKG
RFTISRDNAKNSLYLQMNSLRAEDTAVYYCARRGITTFYWGQG

FIGURE 13

SEQ ID NO:14
VM1013 LC
GCCATCCAGTTGACCCAGTCTCCATCCTCCCTGTCTGCATCTGTAGGAGACAGAGTCACCATCACT
TGCAAGTCCAGTCAAAGTGTTTTATACAGTGCAGTGGAGAAGAACTACTTGGCCTGGTACCAGCA
GAAACCTGGCCAGGCTCCCAGGCTCCTCATCTATTGGGCATCCACTAGGGAAAGGGGGGTCCCAT
CAAGGTTCAGCGGCAGTGGATCTGGGACAGATTTCACTCTCACCATCAGCAGCCTGCAGCCTGAA
GATTTTGCAACTTATTACTGTAAGCAATACCTCTCCTCGTGGACGTTCGGCCAAGGG

SEQ ID NO:30
VM1013 LC
AIQLTQSPSSLSASVGDRVTITCKSSQSVLYSAVEKNYLAWYQQKPGQAPRLLIYWASTRERGVPSRFS
GSGSGTDFTLTISSLQPEDFATYYCKQYLSSWTFGQG

SEQ ID NO:46
VM1013 HC
CAGGTGCAGCTGCAGGAGTCGGGCCCAGGACTGGTGAAGCCTTCACAGACCCTGTCCCTCACCTG
CACTGTCTCTGGCTACGTTTTTACTAGCTACTGGCTGCACTGGATCCGCCAGCCCCCAGGGAAGGG
GCTGGAGTGGATTGGTTACATTAATCCTAGGAATGATTATACTGAGTACAATCGGATTTTCAAGGG
GAGATTCACCATCTCCAGAGACAACGCCAAGAACTCACTGTATCTGCAAATGAACAGCCTGAGAG
CCGAGGACACGGCTGTGTATTACTGTGCGAGAAGGGGGATTACTACGTTCTACTGGGGCCAGGGA

SEQ ID NO:62
VM1013 HC
QVQLQESGPGLVKPSQTLSLTCTVSGYVFTSYWLHWIRQPPGKGLEWIGYINPRNDYTEYNRIFKGRFT
ISRDNAKNSLYLQMNSLRAEDTAVYYCARRGITTFYWGQG

FIGURE 14

SEQ ID NO:15
VM1014 LC
GAAATTGTGTTGACACAGTCTCCAGCCACCCTGGCCTTGTCCCCTGGGGAAAAAGCCCCCCTCTCC
TGGAAGTCCAGTCAAAGTGTTTTATACAGTGGAGTGGAAAAGAACTACTTGGCCTGGTATCAGCA
GAAACCAGGGAAAGCTCCTAAGCTCCTGATCTATTGGGCATCCACTAGGGAAAGGGGGGTCCCCT
CCAGGTTCAGTGGCAGTGGATCTGGGACAGATTTCACTCTCACCATCAGCAGCCTGCAAGCTGAA
GATTTTGCAACTTATTACTGTAAGCAATACCTCTCCTCGTGGACGTTCGGCCAAGGG

SEQ ID NO:31
VM1014 LC
EIVLTQSPATLALSPGEKAPLSWKSSQSVLYSGVEKNYLAWYQQKPGKAPKLLIYWASTRERGVPSRF
SGSGSGTDFTLTISSLQAEDFATYYCKQYLSSWTFGQG

SEQ ID NO:47
VM1014 HC
CAGGTTCAGCTGGTGCAGTCTGGAGCTGAGGTGAAGAAGCCTGGGGCTACAGTGAAAATCTCCTG
CAAGGTTTCTGGCTACGTTTTTACTAGCTACTGGCTGCACTGGATCCGCCAGCCCCCAGGGAAGGG
GCTGGAGTGGATTGGTTACATTAATCCTAGGAATGATTATACTGAGTACAATCGGATTTTCAAGGG
GAGAGTCACGATTACCGCGGACAAATCCACGAGCACAGCCTACATGGAGCTGAGCAGCCTGAGAT
CTGAGGACACGGCCGTGTATTACTGTGCGAGAAGGGGGATTACTACGTTCTACTGGGGCCAGGGA

SEQ ID NO:63
VM1014 HC
QVQLVQSGAEVKKPGATVKISCKVSGYVFTSYWLHWIRQPPGKGLEWIGYINPRNDYTEYNRIFKGRV
TITADKSTSTAYMELSSLRSEDTAVYYCARRGITTFYWGQG

FIGURE 15

SEQ ID NO:16
VM1015 LC
GAAATTGTGTTGACACAGTCTCCAGCCACCCTGGCCTTGTCCCCTGGGGAAAAAGCCCCCCTCTCC
TGGAAGTCCAGTCAAAGTGTTTTATACAGTGGAGTGGAAAAGAACTACTTGGCCTGGTATCAGCA
GAAACCAGGGAAAGCTCCTAAGCTCCTGATCTATTGGGCATCCACTAGGGAAAGGGGGGTCCCCT
CCAGGTTCAGTGGCAGTGGATCTGGGACAGATTTCACTCTCACCATCAGCAGCCTGCAAGCTGAA
GATTTTGCAACTTATTACTGTAAGCAATACCTCTCCTCGTGGACGTTCGGCCAAGGG

SEQ ID NO:32
VM1015 LC
EIVLTQSPATLALSPGEKAPLSWKSSQSVLYSGVEKNYLAWYQQKPGKAPKLLIYWASTRERGVPSRF
SGSGSGTDFTLTISSLQAEDFATYYCKQYLSSWTFGQG

SEQ ID NO:48
VM1015 HC
GAAGTGCAGCTGGTGCAGTCTGGACCAGAAGTGAAAAAGCCCGGGGAGTCTCTGAGGATCTCCTG
TAAGGGTTCTGGCTACGTTTTTACTAGCTACTGGCTGCACTGGGTGCGACAGGCCCCTGGACAAGG
GCTTGAGTGGATGGGTTACATTAATCCTAGGAATGATTATACTGAGTACAATCGGATTTTCAAGGG
GAGAGTCACCATCTCAGCCGACAAGTCCATCAACACCGCCTACCTGCAGTGGAGCAGCCTGAAGG
CCTCGGACACCGCCATGTATTACTGTGCGAGAAGGGGGATTACTACGTTCTACTGGGGCCAGGGA

SEQ ID NO:64
VM1015 HC
EVQLVQSGPEVKKPGESLRISCKGSGYVFTSYWLHWVRQAPGQGLEWMGYINPRNDYTEYNRIFKGR
VTISADKSINTAYLQWSSLKASDTAMYYCARRGITTFYWGQG

FIGURE 16

| Clone | ELISA OD 450 |
|---|---|
| VM1000 | 0.5174 |
| VM1001 | 0.3856 |
| VM1002 | 0.4953 |
| VM1003 | 0.5600 |
| VM1004 | 0.4437 |
| VM1005 | 0.3725 |
| VM1006 | 0.6377 |
| VM1007 | 0.5379 |
| VM1008 | 0.6700 |
| VM1009 | 0.5968 |
| VM1010 | 0.6998 |
| VM1011 | 0.1500 |

FIGURE 17

| Clone | ELISA OD 450 |
|---|---|
| VM006G | 20.00 |
| VM006H | 5.00 |
| VM1000 | 0.50 |
| VM1001 | 0.22 |
| VM1002 | 0.33 |
| VM1003 | 034 |
| VM1004 | 0.80 |
| VM1005 | 19.30 |
| VM1006 | 0.30 |
| VM1007 | 1.00 |
| VM1008 | 1.50 |
| VM1009 | 0.45 |
| VM1010 | 4.80 |
| VM1011 | 0.25 |
| VM1012 | 1.50 |
| VM1013 | 2.40 |
| VM1014 | 0.40 |
| VM1015 | 0.80 |

FIGURE 18

| Clone | Daudi Internalization by FACS, % Shift |
|---|---|
| BA006G | 74.21% |
| VM1000 | 85.93% |
| VM1001 | 86.42% |
| VM1002 | 84.60% |
| VM1003 | 70.80% |
| VM1004 | 87.07% |
| VM1005 | 86.39% |
| VM1006 | 88.33% |
| VM1007 | 85.00% |
| VM1008 | 69.44% |
| VM1009 | 69.44% |
| VM1010 | 65.73% |
| VM1011 | 87.13% |
| VM1012 | 87.51% |
| VM1013 | 88.82% |
| VM1014 | 85.38% |
| VM1015 | 86.60% |

FIGURE 20

| Clone | KD (nM) | Daudi Internalization by Confocal (RMF) |
|---|---|---|
| LL2 (mouse Mab) | 20.00 | ND |
| Control | 5.00 | ~10 |
| VM1000 | 0.50 | ~100 |
| VM1001 | 0.22 | ~100 |
| VM1002 | 0.33 | ~150 |
| VM1003 | 0.34 | ~150 |
| VM1004 | 0.80 | ~100 |
| VM1006 | 2.70 | ~200 |
| VM1007 | 1.00 | ~200 |
| VM1011 | 0.26 | ~200 |

FIGURE 21

| Antibody | Yield (mg/l) |
|---|---|
| Control | 276.2 |
| Antibody 1 | 219.8 |
| Antibody 2 | 255.4 |
| Antibody 3 | 221.7 |
| trastuzumab | 265 |

FIGURE 24

SEQUENCE LISTING

<160> NUMBER OF SEQ ID NOS: 64

<210> SEQ ID NO 1
<211> LENGTH: 318
<212> TYPE: DNA
<213> ORGANISM: Artificial Sequence
<220> FEATURE:
<223> OTHER INFORMATION: antibody

<400> SEQUENCE: 1
gaaattgtgt tgacacagtc tccagccacc ctgtctttgt ctccagggga aagagccacc    60
ctctcctgca agtccagtca agtgttttta tacagtgcag tggagaagaa ctacttggcc   120
tggtatcagc agaaaccagg gaaagctcct aagctcctga tctattgggc atccactagg   180 gaaaggggg tcccatcaag gttcagtgga agtggatctg ggacagattt tactttcacc   240
atcagcagcc tgcagcctga agatattgca acatattact gtaagcaata cctctcctcg   300
tggacgttcg gccaaggg                                                 318

<210> SEQ ID NO 2
<211> LENGTH: 318
<212> TYPE: DNA
<213> ORGANISM: Artificial Sequence
<220> FEATURE:
<223> OTHER INFORMATION: antibody

<400> SEQUENCE: 2
gaaattgtgt tgacacagtc tccagccacc ctgtctttgt ctccagggga aagagccacc    60
ctctcctgca agtccagtca agtgttttta tacagtgcag tggagaagaa ctacttggcc   120
tggtaccagc agaaacctgg ccaggctccc aggctcctca tctattgggc atccactagg   180
gaaaggggga tcccagacag gttcagtggc agtgggtctg ggacagactt cactctcacc   240
atcagcagac tggagcctga agattttgca gtgtattact gtaagcaata cctctcctcg   300
tggacgttcg gccaaggg                                                 318

<210> SEQ ID NO 3
<211> LENGTH: 318
<212> TYPE: DNA
<213> ORGANISM: Artificial Sequence
<220> FEATURE:
<223> OTHER INFORMATION: antibody

<400> SEQUENCE: 3
gaaattgtgt tgacacagtc tccagccacc ctgtctttgt ctccagggga aagagccacc    60
ctctcctgca agtccagtca agtgttttta tacagtgcag tggagaagaa ctacttggcc   120
tggtaccagc agaaacctgg ccaggctccc aggctcctca tctattgggc atccactagg   180
gaaaggggga tcccagacag gttcagtggc agtgggtctg ggacagactt cactctcacc   240
atcagcagac tggagcctga agattttgca gtgtattact gtaagcaata cctctcctcg   300
tggacgttcg gccaaggg                                                 318

<210> SEQ ID NO 4
<211> LENGTH: 318
<212> TYPE: DNA
<213> ORGANISM: Artificial Sequence
<220> FEATURE:
<223> OTHER INFORMATION: antibody

<400> SEQUENCE: 4
gaaattgtgt tgacacagtc tccagccacc ctgtctttgt ctccagggga aagagccacc    60

```
ctctcctgca agtccagtca aagtgtttta tacagtgcag tggagaagaa ctacttggcc      120
tggtaccagc agaaacctgg ccaggctccc aggctcctca tctattgggc atccactagg      180
gaaaggggga tcccagacag gttcagtggc agtgggtctg ggacagactt cactctcacc      240
atcagcagac tggagcctga agattttgca gtgtattact gtaagcaata cctctcctcg      300
tggacgttcg gccaaggg                                                   318

<210> SEQ ID NO 5
<211> LENGTH: 318
<212> TYPE: DNA
<213> ORGANISM: Artificial Sequence
<220> FEATURE:
<223> OTHER INFORMATION: antibody

<400> SEQUENCE: 5
gaaattgtgt tgacacagtc tccagccacc ctgtctttgt ctccagggga aagagccacc       60
ctctcctgca gtccagtca aagtgtttta tacagtgcag tggagaagaa ctacttggcc      120
tggtatcagc agaaaccagg gaaagctcct aagctcctga tctattgggc atccactagg      180
gaaaggggga tcccagacag gttcagtggc agtgggtctg ggacagactt cactctcacc      240
atcagcagac tggagcctga agattttgca gtgtattact gtaagcaata cctctcctcg      300
tggacgttcg gccaaggg                                                   318

<210> SEQ ID NO 6
<211> LENGTH: 318
<212> TYPE: DNA
<213> ORGANISM: Artificial Sequence
<220> FEATURE:
<223> OTHER INFORMATION: antibody

<400> SEQUENCE: 6
gccatccagt tgacccagtc tccatcctcc ctgtctgcat ctgtaggaga cagagtcacc       60
atcacttgca agtccagtca aagtgtttta tacagtgcag tggagaagaa ctacttggcc      120
tggtaccagc agaaacctgg ccaggctccc aggctcctca tctattgggc atccactagg      180 gaaaggggggg tccatcaag gttcagcggc agtggatctg ggacagattt cactctcacc      240
atcagcagcc tgcagcctga agattttgca acttattact gtaagcaata cctctcctcg      300
tggacgttcg gccaaggg                                                   318

<210> SEQ ID NO 7
<211> LENGTH: 318
<212> TYPE: DNA
<213> ORGANISM: Artificial Sequence
<220> FEATURE:
<223> OTHER INFORMATION: antibdy

<400> SEQUENCE: 7
gacatccaga tgacccagtc tccatcctcc ctgtctgcat ctgtaggaga cagagtcacc       60
atcacttgca agtccagtca aagtgtttta tacagtgcag tggagaagaa ctacttggcc      120
tggtatcagc agaaaccagg gaaagctcct aagctcctga tctattgggc atccactagg      180
gaaaggggga tcccagacag gttcagtggc agtgggtctg ggacagactt cactctcacc      240
atcagcagac tggagcctga agattttgca gtgtattact gtaagcaata cctctcctcg      300
tggacgttcg gccaaggg                                                   318

<210> SEQ ID NO 8
```

```
<211> LENGTH: 318
<212> TYPE: DNA
<213> ORGANISM: Artificial Sequence
<220> FEATURE:
<223> OTHER INFORMATION: antibody

<400> SEQUENCE: 8
gccatccagt tgacccagtc tccatcctcc ctgtctgcat ctgtaggaga cagagtcacc    60
atcacttgca agtccagtca aagtgtttta tacagtgcag tggagaagaa ctacttggcc   120
tggtatcagc agaaaccagg gaaagctcct aagctcctga tctattgggc atccactagg   180 gaaaggggg tcccctcgag gttcagtggc agtggatctg ggacagattt cacctttacc   240
atcagtagcc tggaagctga agatgctgca acatattact gtaagcaata cctctcctcg   300
tggacgttcg gccaaggg                                                 318

<210> SEQ ID NO 9
<211> LENGTH: 318
<212> TYPE: DNA
<213> ORGANISM: Artificial Sequence
<220> FEATURE:
<223> OTHER INFORMATION: antibody

<400> SEQUENCE: 9
gacatccaga tgacccagtc tccatcctcc ctgtctgcat ctgtaggaga cagagtcacc    60
atcacttgca agtccagtca aagtgtttta tacagtgcag tggagaagaa ctacttggcc   120
tggtaccagc agaaacctgg ccaggctccc aggctcctca tctattgggc atccactagg   180
gaaaggggga tcccagacag gttcagtggc agtgggtctg ggacagactt cactctcacc   240
atcagcagac tggagcctga agattttgca gtgtattact gtaagcaata cctctcctcg   300
tggacgttcg gccaaggg                                                 318

<210> SEQ ID NO 10
<211> LENGTH: 318
<212> TYPE: DNA
<213> ORGANISM: Artificial Sequence
<220> FEATURE:
<223> OTHER INFORMATION: antibody

<400> SEQUENCE: 10
gaaattgtgt tgacacagtc tccagccacc ctgtctttgt ctccagggga aagagccacc    60
ctctcctgca agtccagtca aagtgtttta tacagtgcag tggagaagaa ctacttggcc   120
tggtatcagc agaaaccagg gaaagctcct aagctcctga tctattgggc atccactagg   180 gaaaggggg tcccctcgag gttcagtggc agtggatctg ggacagattt cacctttacc   240
atcagtagcc tggaagctga agatgctgca acatattact gtaagcaata cctctcctcg   300
tggacgttcg gccaaggg                                                 318

<210> SEQ ID NO 11
<211> LENGTH: 318
<212> TYPE: DNA
<213> ORGANISM: Artificial Sequence
<220> FEATURE:
<223> OTHER INFORMATION: antibody

<400> SEQUENCE: 11
gaaattgtgt tgacacagtc tccagccacc ctgtctttgt ctccagggga aagagccacc    60
ctctcctgca agtccagtca aagtgtttta tacagtgcag tggagaagaa ctacttggcc   120
tggtatcagc agaaaccagg gaaagctcct aagctcctga tctattgggc atccactagg   180
```

| gaaaggggg tcccatcaag gttcagtgga agtggatctg ggacagattt tactttcacc | 240 |
| atcagcagcc tgcagcctga agatattgca acatattact gtaagcaata cctctcctcg | 300 |
| tggacgttcg gccaaggg | 318 |

<210> SEQ ID NO 12
<211> LENGTH: 318
<212> TYPE: DNA
<213> ORGANISM: Artificial Sequence
<220> FEATURE:
<223> OTHER INFORMATION: antibody

<400> SEQUENCE: 12

| gaaattgtgt tgacacagtc tccagccacc ctgtctttgt ctccagggga aagagccacc | 60 |
| ctctcctgca gtccagtca aagtgtttta tacagtgcag tggagaagaa ctacttggcc | 120 |
| tggtaccagc agaaacctgg ccaggctccc aggctcctca tctattgggc atccactagg | 180 |
| gaaaggggga tcccagacag gttcagtggc agtgggtctg gacagacttc cactctcacc | 240 |
| atcagcagac tggagcctga agattttgca gtgtattact gtaagcaata cctctcctcg | 300 |
| tggacgttcg gccaaggg | 318 |

<210> SEQ ID NO 13
<211> LENGTH: 318
<212> TYPE: DNA
<213> ORGANISM: Artificial Sequence
<220> FEATURE:
<223> OTHER INFORMATION: antibody

<400> SEQUENCE: 13

| gaaattgtgt tgacacagtc tccagccacc ctgtctgtgt ctccagggga aagagccacc | 60 |
| ctctcctgca gtccagtca aagtgtttta tacagtgcag tggagaagaa ctacttggcc | 120 |
| tggtaccagc agaaacctgg ccaggctccc aggctcctca tctattgggc atccactagg | 180 |
| gaaaggggg tcccatcaag gttcagtgga agtggatctg ggacagattt tactttcacc | 240 |
| atcagcagcc tgcagcctga agatattgca acatattact gtaagcaata cctctcctcg | 300 |
| tggacgttcg gccaaggg | 318 |

<210> SEQ ID NO 14
<211> LENGTH: 318
<212> TYPE: DNA
<213> ORGANISM: Artificial Sequence
<220> FEATURE:
<223> OTHER INFORMATION: antibody

<400> SEQUENCE: 14

| gccatccagt tgacccagtc tccatcctcc ctgtctgcat ctgtaggaga cagagtcacc | 60 |
| atcacttgca gtccagtca aagtgtttta tacagtgcag tggagaagaa ctacttggcc | 120 |
| tggtaccagc agaaacctgg ccaggctccc aggctcctca tctattgggc atccactagg | 180 |
| gaaaggggg tcccatcaag gttcagcggc agtggatctg ggacagattt cactctcacc | 240 |
| atcagcagcc tgcagcctga agattttgca acttattact gtaagcaata cctctcctcg | 300 |
| tggacgttcg gccaaggg | 318 |

<210> SEQ ID NO 15
<211> LENGTH: 318
<212> TYPE: DNA
<213> ORGANISM: Artificial Sequence
<220> FEATURE:

<223> OTHER INFORMATION: antibody

<400> SEQUENCE: 15

```
gaaattgtgt tgacacagtc tccagccacc ctggccttgt ccctggggga aaaagccccc    60
ctctcctgga agtccagtca aagtgtttta tacagtggag tggaaaagaa ctacttggcc   120
tggtatcagc agaaaccagg gaaagctcct aagctcctga tctattgggc atccactagg   180
gaaaggggg tccctccag gttcagtggc agtggatctg ggacagattt cactctcacc   240
atcagcagcc tgcaagctga agattttgca acttattact gtaagcaata cctctcctcg   300
tggacgttcg gccaaggg                                                318
```

<210> SEQ ID NO 16
<211> LENGTH: 318
<212> TYPE: DNA
<213> ORGANISM: Artificial Sequence
<220> FEATURE:
<223> OTHER INFORMATION: antibody

<400> SEQUENCE: 16

```
gaaattgtgt tgacacagtc tccagccacc ctggccttgt ccctggggga aaaagccccc    60
ctctcctgga agtccagtca aagtgtttta tacagtggag tggaaaagaa ctacttggcc   120
tggtatcagc agaaaccagg gaaagctcct aagctcctga tctattgggc atccactagg   180
gaaaggggg tccctccag gttcagtggc agtggatctg ggacagattt cactctcacc   240
atcagcagcc tgcaagctga agattttgca acttattact gtaagcaata cctctcctcg   300
tggacgttcg gccaaggg                                                318
```

<210> SEQ ID NO 17
<211> LENGTH: 106
<212> TYPE: PRT
<213> ORGANISM: Artificial Sequence
<220> FEATURE:
<223> OTHER INFORMATION: antibody

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Val Leu Tyr Ser
            20                  25                  30

Ala Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Lys Gln
                85                  90                  95

Tyr Leu Ser Ser Trp Thr Phe Gly Gln Gly
            100                 105

<210> SEQ ID NO 18
<211> LENGTH: 106
<212> TYPE: PRT
<213> ORGANISM: Artificial Sequence
<220> FEATURE:
<223> OTHER INFORMATION:
    EIVLTQSPATLSLSPGERATLSCKSSQSVLYSAVEKNYLAWYQQKPGQAPRLLIYWASTRERGIP
    DRFSGSGSGTDFTLTISRLEPEDFAVYYCKQYLSSWTFGQG
```

```
<400> SEQUENCE: 18

Glu Ile Val Leu Thr Gln Ser Pro Ala Thr Leu Ser Leu Ser Pro Gly
1               5                  10                  15

Glu Arg Ala Thr Leu Ser Cys Lys Ser Ser Gln Ser Val Leu Tyr Ser
                20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Ile
        50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
                100                 105

<210> SEQ ID NO 19
<211> LENGTH: 106
<212> TYPE: PRT
<213> ORGANISM: Artificial Sequence
<220> FEATURE:
<223> OTHER INFORMATION: antibody

<400> SEQUENCE: 19

Glu Ile Val Leu Thr Gln Ser Pro Ala Thr Leu Ser Leu Ser Pro Gly
1               5                  10                  15

Glu Arg Ala Thr Leu Ser Cys Lys Ser Ser Gln Ser Val Leu Tyr Ser
                20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Ile
        50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
                100                 105

<210> SEQ ID NO 20
<211> LENGTH: 106
<212> TYPE: PRT
<213> ORGANISM: Artificial Sequence
<220> FEATURE:
<223> OTHER INFORMATION: antibody

<400> SEQUENCE: 20

Glu Ile Val Leu Thr Gln Ser Pro Ala Thr Leu Ser Leu Ser Pro Gly
1               5                  10                  15

Glu Arg Ala Thr Leu Ser Cys Lys Ser Ser Gln Ser Val Leu Tyr Ser
                20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Ile
        50                  55                  60

Pro Asp Arg Phe Ser Gly Ser Gly Ser Gly Thr Asp Phe Thr Leu Thr
65                  70                  75                  80
```

```
Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: antibody

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Lys Ser Gln Ser Val Leu Tyr Ser
                20                  25                  30

Ala Val Glu Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Arg Gly Ile
        50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
            100                 105

<210> SEQ ID NO 22
<211> LENGTH: 106
<212> TYPE: PRT
<213> ORGANISM: Artificial Sequence
<220> FEATURE:
<223> OTHER INFORMATION: antibody

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Lys Ser Gln Ser Val Leu Tyr Ser
                20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Tyr Leu Ser Ser Trp Thr Phe Gly Gln Gly
            100                 105

<210> SEQ ID NO 23
<211> LENGTH: 106
<212> TYPE: PRT
<213> ORGANISM: Artificial Sequence
<220> FEATURE:
<223> OTHER INFORMATION: antibody

<400> SEQUENCE: 23

Asp Ile Gln Met Thr Gln Ser Pro Ser Ser Leu Ser Ala Ser Val Gly
```

```
                1               5                  10                  15
Asp Arg Val Thr Ile Thr Cys Lys Ser Ser Gln Ser Val Leu Tyr Ser
                20                  25                  30

Ala Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
                100                 105

<210> SEQ ID NO 24
<211> LENGTH: 106
<212> TYPE: PRT
<213> ORGANISM: Artificial Sequence
<220> FEATURE:
<223> OTHER INFORMATION: antibody

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
                20                  25                  30

Ala Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Lys Gln
                85                  90                  95

Tyr Leu Ser Ser Trp Thr Phe Gly Gln Gly
                100                 105

<210> SEQ ID NO 25
<211> LENGTH: 106
<212> TYPE: PRT
<213> ORGANISM: Artificial Sequence
<220> FEATURE:
<223> OTHER INFORMATION: antibody

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
                20                  25                  30

Ala Val Glu Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Arg Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Lys Gln
                85                  90                  95
```

Tyr Leu Ser Ser Trp Thr Phe Gly Gln Gly
            100                 105

<210> SEQ ID NO 26
<211> LENGTH: 106
<212> TYPE: PRT
<213> ORGANISM: Artificial Sequence
<220> FEATURE:
<223> OTHER INFORMATION: antibody

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Val Leu Tyr Ser
            20                  25                  30

Ala Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Lys Gln
                85                  90                  95

Tyr Leu Ser Ser Trp Thr Phe Gly Gln Gly
            100                 105

<210> SEQ ID NO 27
<211> LENGTH: 106
<212> TYPE: PRT
<213> ORGANISM: Artificial Sequence
<220> FEATURE:
<223> OTHER INFORMATION: antibody

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Val Leu Tyr Ser
            20                  25                  30

Ala Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Lys Gln
                85                  90                  95

Tyr Leu Ser Ser Trp Thr Phe Gly Gln Gly
            100                 105

<210> SEQ ID NO 28
<211> LENGTH: 106
<212> TYPE: PRT
<213> ORGANISM: Artificial Sequence
<220> FEATURE:
<223> OTHER INFORMATION: antibody

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Val Leu Tyr Ser

```
            20                  25                  30
Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Ile
        50                  55                  60

Pro Asp Arg Phe Ser Gly Ser Gly Ser Gly Thr Asp Phe Thr Leu Thr
 65                 70                  75                  80

Ile Ser Arg Leu Glu Pro Glu Asp Phe Ala Val Tyr Tyr Cys Lys Gln
                85                  90                  95

Tyr Leu Ser Ser Trp Thr Phe Gly Gln Gly
            100                 105

<210> SEQ ID NO 29
<211> LENGTH: 106
<212> TYPE: PRT
<213> ORGANISM: Artificial Sequence
<220> FEATURE:
<223> OTHER INFORMATION: antibody

<400> SEQUENCE: 29

Glu Ile Val Leu Thr Gln Ser Pro Ala Thr Leu Ser Val Ser Pro Gly
 1               5                  10                  15

Glu Arg Ala Thr Leu Ser Cys Lys Ser Gln Ser Val Leu Tyr Ser
            20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Val
        50                  55                  60

Pro Ser Arg Phe Ser Gly Ser Gly Ser Gly Thr Asp Phe Thr Phe Thr
 65                 70                  75                  80

Ile Ser Ser Leu Gln Pro Glu Asp Ile Ala Thr Tyr Tyr Cys Lys Gln
                85                  90                  95

Tyr Leu Ser Ser Trp Thr Phe Gly Gln Gly
            100                 105

<210> SEQ ID NO 30
<211> LENGTH: 106
<212> TYPE: PRT
<213> ORGANISM: Artificial Sequence
<220> FEATURE:
<223> OTHER INFORMATION: antibody

<400> SEQUENCE: 30

Ala Ile Gln Leu Thr Gln Ser Pro Ser Ser Leu Ser Ala Ser Val Gly
 1               5                  10                  15

Asp Arg Val Thr Ile Thr Cys Lys Ser Gln Ser Val Leu Tyr Ser
            20                  25                  30

Ala Val Glu Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Arg Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Lys Gln
                85                  90                  95

Tyr Leu Ser Ser Trp Thr Phe Gly Gln Gly
            100                 105
```

<210> SEQ ID NO 31
<211> LENGTH: 106
<212> TYPE: PRT
<213> ORGANISM: Artificial Sequence
<220> FEATURE:
<223> OTHER INFORMATION: antibody

<400> SEQUENCE: 31

```
Glu Ile Val Leu Thr Gln Ser Pro Ala Thr Leu Ala Leu Ser Pro Gly
1               5                   10                  15

Glu Lys Ala Pro Leu Ser Trp Lys Ser Ser Gln Ser Val Leu Tyr Ser
            20                  25                  30

Gly Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Ala Glu Asp Phe Ala Thr Tyr Tyr Cys Lys Gln
                85                  90                  95

Tyr Leu Ser Ser Trp Thr Phe Gly Gln Gly
            100                 105
```

<210> SEQ ID NO 32
<211> LENGTH: 106
<212> TYPE: PRT
<213> ORGANISM: Artificial Sequence
<220> FEATURE:
<223> OTHER INFORMATION: antibody

<400> SEQUENCE: 32

```
Glu Ile Val Leu Thr Gln Ser Pro Ala Thr Leu Ala Leu Ser Pro Gly
1               5                   10                  15

Glu Lys Ala Pro Leu Ser Trp Lys Ser Ser Gln Ser Val Leu Tyr Ser
            20                  25                  30

Gly Val Glu Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Arg Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Ala Glu Asp Phe Ala Thr Tyr Tyr Cys Lys Gln
                85                  90                  95

Tyr Leu Ser Ser Trp Thr Phe Gly Gln Gly
            100                 105
```

<210> SEQ ID NO 33
<211> LENGTH: 327
<212> TYPE: DNA
<213> ORGANISM: Artificial Sequence
<220> FEATURE:
<223> OTHER INFORMATION: antibody

<400> SEQUENCE: 33

```
caggttcagc tggtgcagtc tggagctgag gtgaagaagc ctggggcctc agtgaaggtc      60
tcctgcaagg cttctggcta cgttttact  agctactggc tgcactggat caggcagtcc     120
ccatcgagag gccttgagtg gctgggttac attaatccta ggaatgatta tactgagtac     180
aatcggattt tcaaggggag actcaccatc tccaaggaca cctccaaaaa ccaggtggtc     240
```

```
cttacaatga ccaacatgga ccctgtggac acagccacgt attactgtgc aagaaggggg      300
attactacgt tctactgggg ccaggga                                          327

<210> SEQ ID NO 34
<211> LENGTH: 327
<212> TYPE: DNA
<213> ORGANISM: Artificial Sequence
<220> FEATURE:
<223> OTHER INFORMATION: antibody

<400> SEQUENCE: 34
caggttcagc tggtgcagtc tggagctgag gtgaagaagc tggggcctc agtgaaggtc       60 tcctgcaagg cttctggcta cgttttact agctactggc tgcactggat caggcagtcc     120
ccatcgagag gccttgagtg gctgggttac attaatccta ggaatgatta tactgagtac    180
aatcggattt tcaaggggag actcaccatc tccaaggaca cctccaaaaa ccaggtggtc    240
cttacaatga ccaacatgga ccctgtggac acagccacgt attactgtgc aagaaggggg    300
attactacgt tctactgggg ccaggga                                          327

<210> SEQ ID NO 35
<211> LENGTH: 327
<212> TYPE: DNA
<213> ORGANISM: Artificial Sequence
<220> FEATURE:
<223> OTHER INFORMATION: antibody

<400> SEQUENCE: 35
gaagtgcagc tggtgcagtc tggagcagag gtgaaaaagc ccggggagtc tctgaggatc      60
tcctgtaagg gttctggcta cgttttact agctactggc tgcactgggt gcgacaggcc     120
cctggacaag ggcttgagtg gatgggttac attaatccta ggaatgatta tactgagtac    180
aatcggattt tcaaggggag agtcacgatt accgcggaca atccacgag cacagcctac     240 atggagctga gcagcctgag atctgaggac acggccgtgt attactgtgc gagaaggggg    300
attactacgt tctactgggg ccaggga                                          327

<210> SEQ ID NO 36
<211> LENGTH: 327
<212> TYPE: DNA
<213> ORGANISM: Artificial Sequence
<220> FEATURE:
<223> OTHER INFORMATION: antibody

<400> SEQUENCE: 36
gaggtccagc tggtacagtc tggggctgag gtgaagaagc ctgggctac agtgaaaatc       60 tcctgcaagg tttctggcta cgttttact agctactggc tgcactggat caggcagtcc     120
ccatcgagag gccttgagtg gctgggttac attaatccta ggaatgatta tactgagtac    180
aatcggattt tcaaggggag atttgtcttc tccttggaca cctctgtcag cacggcatat    240
ctgcagatct gcagcctaaa ggctgaggac actgccgtgt attactgtgc gagaaggggg    300
attactacgt tctactgggg ccaggga                                          327

<210> SEQ ID NO 37
<211> LENGTH: 327
<212> TYPE: DNA
<213> ORGANISM: Artificial Sequence
<220> FEATURE:
<223> OTHER INFORMATION: antibody
```

<400> SEQUENCE: 37

```
gaggtccagc tggtacagtc tggggctgag gtgaagaagc ctggggctac agtgaaaatc      60
tcctgcaagg tttctggcta cgttttact agctactggc tgcactggat caggcagtcc     120
ccatcgagag gccttgagtg gctgggttac attaatccta ggaatgatta tactgagtac    180
aatcggattt tcaaggggag atttgtcttc tccttggaca cctctgtcag cacggcatat    240
ctgcagatct gcagcctaaa ggctgaggac actgccgtgt attactgtgc gagaaggggg    300
attactacgt tctactgggg ccaggga                                         327
```

<210> SEQ ID NO 38
<211> LENGTH: 327
<212> TYPE: DNA
<213> ORGANISM: Artificial Sequence
<220> FEATURE:
<223> OTHER INFORMATION: antibody

<400> SEQUENCE: 38

```
gaggtccagc tggtacagtc tggggctgag gtgaagaagc ctggggctac agtgaaaatc      60
tcctgcaagg tttctggcta cgttttact agctactggc tgcactggat caggcagtcc     120
ccatcgagag gccttgagtg gctgggttac attaatccta ggaatgatta tactgagtac    180
aatcggattt tcaaggggag atttgtcttc tccttggaca cctctgtcag cacggcatat    240
ctgcagatct gcagcctaaa ggctgaggac actgccgtgt attactgtgc gagaaggggg    300
attactacgt tctactgggg ccaggga                                         327
```

<210> SEQ ID NO 39
<211> LENGTH: 327
<212> TYPE: DNA
<213> ORGANISM: Artificial Sequence
<220> FEATURE:
<223> OTHER INFORMATION: antibody

<400> SEQUENCE: 39

```
caggttcagc tggtgcagtc tggagctgag gtgaagaagc ctggggcctc agtgaaggtc      60
tcctgcaagg cttctggcta cgttttact agctactggc tgcactggat caggcagtcc     120
ccatcgagag gccttgagtg gctgggttac attaatccta ggaatgatta tactgagtac    180
aatcggattt tcaaggggag atttgtcttc tccttggaca cctctgtcag cacggcatat    240
ctgcagatct gcagcctaaa ggctgaggac actgccgtgt attactgtgc gagaaggggg    300
attactacgt tctactgggg ccaggga                                         327
```

<210> SEQ ID NO 40
<211> LENGTH: 327
<212> TYPE: DNA
<213> ORGANISM: Artificial Sequence
<220> FEATURE:
<223> OTHER INFORMATION: antibody

<400> SEQUENCE: 40

```
caggttcagc tggtgcagtc tggagctgag gtgaagaagc ctggggcctc agtgaaggtc      60
tcctgcaagg cttctggcta cgttttact agctactggc tgcactgggt gcgacaggct     120
cgtggacaac gccttgagtg gataggttac attaatccta ggaatgatta tactgagtac    180
aatcggattt tcaaggggag agtcacgatt accgcggaca atccacgag cacagcctac    240
atggagctga gcagcctgag atctgaggac acggccgtgt attactgtgc gagaaggggg    300
attactacgt tctactgggg ccaggga                                         327
```

<210> SEQ ID NO 41
<211> LENGTH: 327
<212> TYPE: DNA
<213> ORGANISM: Artificial Sequence
<220> FEATURE:
<223> OTHER INFORMATION: antibody

<400> SEQUENCE: 41
caggttcagc tggtgcagtc tggagctgag gtgaagaagc ctggggcctc agtgaaggtc       60
tcctgcaagg cttctggcta cgttttact agctactggc tgcactgggt gcgacaggct      120
cgtggacaac gccttgagtg ataggttac attaatccta ggaatgatta tactgagtac      180
aatcggattt tcaaggggag agtcacgatt accgcggaca atccacgag cacagcctac       240 atggagctga gcagcctgag atctgaggac acggccgtgt attactgtgc gagaaggggg      300
attactacgt tctactgggg ccaggga                                          327

<210> SEQ ID NO 42
<211> LENGTH: 327
<212> TYPE: DNA
<213> ORGANISM: Artificial Sequence
<220> FEATURE:
<223> OTHER INFORMATION: antibody

<400> SEQUENCE: 42
caggttcagc tggtgcagtc tggagctgag gtgaagaagc ctggggcctc agtgaaggtc       60
tcctgcaagg cttctggcta cgttttact agctactggc tgcactggat caggcagtcc      120
ccatcgagag gccttgagtg gctgggttac attaatccta ggaatgatta tactgagtac      180
aatcggattt tcaaggggag atttgtcttc tccttggaca cctctgtcag cacggcatat      240
ctgcagatct gcagcctaaa ggctgaggac actgccgtgt attactgtgc gagaaggggg      300
attactacgt tctactgggg ccaggga                                          327

<210> SEQ ID NO 43
<211> LENGTH: 327
<212> TYPE: DNA
<213> ORGANISM: Artificial Sequence
<220> FEATURE:
<223> OTHER INFORMATION: antibody

<400> SEQUENCE: 43
gaagtgcagc tggtgcagtc tggagcagag gtgaaaaagc ccggggagtc tctgaggatc       60
tcctgtaagg tttctggcta cgttttact agctactggc tgcactggat caggcagtcc      120
ccatcgagag gccttgagtg gctgggttac attaatccta ggaatgatta tactgagtac      180
aatcggattt tcaaggggag attcaccatc tccagagaca cgccaagaa ctcactgtat      240 ctgcaaatga acagcctgag agccgaggac acggctgtgt attactgtgc gagaagggggg     300 attactacgt tctactgggg ccaggga                                          327

<210> SEQ ID NO 44
<211> LENGTH: 327
<212> TYPE: DNA
<213> ORGANISM: Artificial Sequence
<220> FEATURE:
<223> OTHER INFORMATION: antibody

<400> SEQUENCE: 44
caggtgcagc tgcaggagtc gggcccagga ctggtgaagc cttcacagac cctgtccctc       60

```
acctgcactg tctctggcta cgttttact agctactggc tgcactggat ccgccagccc     120
ccagggaagg ggctggagtg gattggttac attaatccta ggaatgatta tactgagtac     180
aatcggattt tcaaggggag agtcacgatt accgcggaca aatccacgag cacagcctac     240
atggagctga gcagcctgag atctgaggac acggccgtgt attactgtgc gagaaggggg     300
attactacgt tctactgggg ccaggga                                        327

<210> SEQ ID NO 45
<211> LENGTH: 327
<212> TYPE: DNA
<213> ORGANISM: Artificial Sequence
<220> FEATURE:
<223> OTHER INFORMATION: antibody

<400> SEQUENCE: 45
caggttcagc tggtgcagtc tggagctgag gtgaagaagc ctggggcctc agtgaaggtc      60
tcctgcaagg cttctggcta cgttttact agctactggc tgcactgggt gcgacaggcc     120
cctggacaag ggcttgagtg gatgggttac attaatccta ggaatgatta tactgagtac     180
aatcggattt tcaaggggag attcaccatc tccagagaca cgccaagaa ctcactgtat     240 ctgcaaatga acagcctgag agccgaggac acggctgtgt attactgtgc gagaaggggg     300
attactacgt tctactgggg ccaggga                                        327

<210> SEQ ID NO 46
<211> LENGTH: 327
<212> TYPE: DNA
<213> ORGANISM: Artificial Sequence
<220> FEATURE:
<223> OTHER INFORMATION: antibody

<400> SEQUENCE: 46
caggtgcagc tgcaggagtc gggcccagga ctggtgaagc cttcacagac cctgtccctc      60
acctgcactg tctctggcta cgttttact agctactggc tgcactggat ccgccagccc     120
ccagggaagg ggctggagtg gattggttac attaatccta ggaatgatta tactgagtac     180
aatcggattt tcaaggggag attcaccatc tccagagaca cgccaagaa ctcactgtat     240 ctgcaaatga acagcctgag agccgaggac acggctgtgt attactgtgc gagaaggggg     300
attactacgt tctactgggg ccaggga                                        327

<210> SEQ ID NO 47
<211> LENGTH: 327
<212> TYPE: DNA
<213> ORGANISM: Artificial Sequence
<220> FEATURE:
<223> OTHER INFORMATION: antibody

<400> SEQUENCE: 47
caggttcagc tggtgcagtc tggagctgag gtgaagaagc ctggggctac agtgaaaatc      60
tcctgcaagg tttctggcta cgttttact agctactggc tgcactggat ccgccagccc     120
ccagggaagg ggctggagtg gattggttac attaatccta ggaatgatta tactgagtac     180
aatcggattt tcaaggggag agtcacgatt accgcggaca aatccacgag cacagcctac     240
atggagctga gcagcctgag atctgaggac acggccgtgt attactgtgc gagaagggggg     300 attactacgt tctactgggg ccaggga                                        327

<210> SEQ ID NO 48
<211> LENGTH: 327
```

<212> TYPE: DNA
<213> ORGANISM: Artificial Sequence
<220> FEATURE:
<223> OTHER INFORMATION: anti

<400> SEQUENCE: 48

```
gaagtgcagc tggtgcagtc tggaccagaa gtgaaaaagc ccggggagtc tctgaggatc    60
tcctgtaagg gttctggcta cgttttact agctactggc tgcactgggt gcgacaggcc   120
cctggacaag gcttgagtg gatgggttac attaatccta ggaatgatta tactgagtac   180
aatcggattt tcaaggggag agtcaccatc tcagccgaca gtccatcaa caccgcctac   240
ctgcagtgga gcagcctgaa ggcctcggac accgccatgt attactgtgc gagaagggg   300
attactacgt tctactgggg ccaggga                                       327
```

<210> SEQ ID NO 49
<211> LENGTH: 109
<212> TYPE: PRT
<213> ORGANISM: Artificial Sequence
<220> FEATURE:
<223> OTHER INFORMATION: antibody

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
            20                  25                  30

Trp Leu His Trp Ile Arg Gln Ser Pro Ser Arg Gly Leu Glu Trp Leu
        35                  40                  45

Gly Tyr Ile Asn Pro Arg Asn Asp Tyr Thr Glu Tyr Asn Arg Ile Phe
    50                  55                  60

Lys Gly Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Arg Gly Ile Thr Thr Phe Tyr Trp Gly Gln Gly
            100                 105
```

<210> SEQ ID NO 50
<211> LENGTH: 109
<212> TYPE: PRT
<213> ORGANISM: Artificial Sequence
<220> FEATURE:
<223> OTHER INFORMATION: antibody

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
            20                  25                  30

Trp Leu His Trp Ile Arg Gln Ser Pro Ser Arg Gly Leu Glu Trp Leu
        35                  40                  45

Gly Tyr Ile Asn Pro Arg Asn Asp Tyr Thr Glu Tyr Asn Arg Ile Phe
    50                  55                  60

Lys Gly Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Arg Gly Ile Thr Thr Phe Tyr Trp Gly Gln Gly
```

<210> SEQ ID NO 51
<211> LENGTH: 109
<212> TYPE: PRT
<213> ORGANISM: Artificial Sequence
<220> FEATURE:
<223> OTHER INFORMATION: antibody

<400> SEQUENCE: 51

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Val Phe Thr Ser Tyr
                20                  25                  30

Trp Leu His Trp Val Arg Gln Ala Pro Gly Gln Gly Leu Glu Trp Met
            35                  40                  45

Gly Tyr Ile Asn Pro Arg Asn Asp Tyr Thr Glu Tyr Asn Arg Ile Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 52
<211> LENGTH: 109
<212> TYPE: PRT
<213> ORGANISM: Artificial Sequence
<220> FEATURE:
<223> OTHER INFORMATION: antibody

<400> SEQUENCE: 52

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Val Phe Thr Ser Tyr
                20                  25                  30

Trp Leu His Trp Ile Arg Gln Ser Pro Ser Arg Gly Leu Glu Trp Leu
            35                  40                  45

Gly Tyr Ile Asn Pro Arg Asn Asp Tyr Thr Glu Tyr Asn Arg Ile Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 53
<211> LENGTH: 109
<212> TYPE: PRT
<213> ORGANISM: Artificial Sequence
<220> FEATURE:
<223> OTHER INFORMATION: antibody

<400> SEQUENCE: 53

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Val Phe Thr Ser Tyr
                20                  25                  30

Trp Leu His Trp Ile Arg Gln Ser Pro Ser Arg Gly Leu Glu Trp Leu
            35                  40                  45

Gly Tyr Ile Asn Pro Arg Asn Asp Tyr Thr Glu Tyr Asn Arg Ile Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 54
<211> LENGTH: 109
<212> TYPE: PRT
<213> ORGANISM: Artificial Sequence
<220> FEATURE:
<223> OTHER INFORMATION: antibody

<400> SEQUENCE: 54

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Val Phe Thr Ser Tyr
                20                  25                  30

Trp Leu His Trp Ile Arg Gln Ser Pro Ser Arg Gly Leu Glu Trp Leu
            35                  40                  45

Gly Tyr Ile Asn Pro Arg Asn Asp Tyr Thr Glu Tyr Asn Arg Ile Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 55
<211> LENGTH: 109
<212> TYPE: PRT
<213> ORGANISM: Artificial Sequence
<220> FEATURE:
<223> OTHER INFORMATION: antibody

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
                20                  25                  30

Trp Leu His Trp Ile Arg Gln Ser Pro Ser Arg Gly Leu Glu Trp Leu
            35                  40                  45

Gly Tyr Ile Asn Pro Arg Asn Asp Tyr Thr Glu Tyr Asn Arg Ile Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Ile Thr Thr Phe Tyr Trp Gly Gln Gly
                100                 105

```
<210> SEQ ID NO 56
<211> LENGTH: 109
<212> TYPE: PRT
<213> ORGANISM: Artificial Sequence
<220> FEATURE:
<223> OTHER INFORMATION: antibody

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
            20                  25                  30

Trp Leu His Trp Val Arg Gln Ala Arg Gly Gln Arg Leu Glu Trp Ile
        35                  40                  45

Gly Tyr Ile Asn Pro Arg Asn Asp Tyr Thr Glu Tyr Asn Arg Ile Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Thr Thr Phe Tyr Trp Gly Gln Gly
            100                 105

<210> SEQ ID NO 57
<211> LENGTH: 109
<212> TYPE: PRT
<213> ORGANISM: Artificial Sequence
<220> FEATURE:
<223> OTHER INFORMATION: antibody

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
            20                  25                  30

Trp Leu His Trp Val Arg Gln Ala Arg Gly Gln Arg Leu Glu Trp Ile
        35                  40                  45

Gly Tyr Ile Asn Pro Arg Asn Asp Tyr Thr Glu Tyr Asn Arg Ile Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Thr Thr Phe Tyr Trp Gly Gln Gly
            100                 105

<210> SEQ ID NO 58
<211> LENGTH: 109
<212> TYPE: PRT
<213> ORGANISM: Artificial Sequence
<220> FEATURE:
<223> OTHER INFORMATION: antibody

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
            20                  25                  30

Trp Leu His Trp Ile Arg Gln Ser Pro Ser Arg Gly Leu Glu Trp Leu
        35                  40                  45
```

Gly Tyr Ile Asn Pro Arg Asn Asp Tyr Thr Glu Tyr Asn Arg Ile Phe
            50                  55                  60

Lys Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Arg Gly Ile Thr Thr Phe Tyr Trp Gly Gln Gly
                100                 105

<210> SEQ ID NO 59
<211> LENGTH: 109
<212> TYPE: PRT
<213> ORGANISM: Artificial Sequence
<220> FEATURE:
<223> OTHER INFORMATION: antibody

<400> SEQUENCE: 59

Glu Val Gln Leu Val Gln Ser Gly Ala Glu Val Lys Lys Pro Gly Glu
 1               5                  10                  15

Ser Leu Arg Ile Ser Cys Lys Val Ser Gly Tyr Val Phe Thr Ser Tyr
                 20                  25                  30

Trp Leu His Trp Ile Arg Gln Ser Pro Ser Arg Gly Leu Glu Trp Leu
             35                  40                  45

Gly Tyr Ile Asn Pro Arg Asn Asp Tyr Thr Glu Tyr Asn Arg Ile Phe
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Ile Thr Thr Phe Tyr Trp Gly Gln Gly
                100                 105

<210> SEQ ID NO 60
<211> LENGTH: 109
<212> TYPE: PRT
<213> ORGANISM: Artificial Sequence
<220> FEATURE:
<223> OTHER INFORMATION: antibody

<400> SEQUENCE: 60

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Val Phe Thr Ser Tyr
                 20                  25                  30

Trp Leu His Trp Ile Arg Gln Pro Pro Gly Lys Gly Leu Glu Trp Ile
             35                  40                  45

Gly Tyr Ile Asn Pro Arg Asn Asp Tyr Thr Glu Tyr Asn Arg Ile Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Thr Thr Phe Tyr Trp Gly Gln Gly
                100                 105

<210> SEQ ID NO 61
<211> LENGTH: 109
<212> TYPE: PRT

```
<213> ORGANISM: Artificial Sequence
<220> FEATURE:
<223> OTHER INFORMATION: antibody

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Ser Tyr
                20                  25                  30

Trp Leu His Trp Val Arg Gln Ala Pro Gly Gln Gly Leu Glu Trp Met
            35                  40                  45

Gly Tyr Ile Asn Pro Arg Asn Asp Tyr Thr Glu Tyr Asn Arg Ile Phe
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 62
<211> LENGTH: 109
<212> TYPE: PRT
<213> ORGANISM: Artificial Sequence
<220> FEATURE:
<223> OTHER INFORMATION: antibody

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Val Phe Thr Ser Tyr
                20                  25                  30

Trp Leu His Trp Ile Arg Gln Pro Pro Gly Lys Gly Leu Glu Trp Ile
            35                  40                  45

Gly Tyr Ile Asn Pro Arg Asn Asp Tyr Thr Glu Tyr Asn Arg Ile Phe
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Thr Thr Phe Tyr Trp Gly Gln Gly
                100                 105

<210> SEQ ID NO 63
<211> LENGTH: 109
<212> TYPE: PRT
<213> ORGANISM: Artificial Sequence
<220> FEATURE:
<223> OTHER INFORMATION: antibody

<400> SEQUENCE: 63

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Val Phe Thr Ser Tyr
                20                  25                  30

Trp Leu His Trp Ile Arg Gln Pro Pro Gly Lys Gly Leu Glu Trp Ile
            35                  40                  45

Gly Tyr Ile Asn Pro Arg Asn Asp Tyr Thr Glu Tyr Asn Arg Ile Phe
        50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Thr Thr Phe Tyr Trp Gly Gln Gly
            100                 105

<210> SEQ ID NO 64
<211> LENGTH: 109
<212> TYPE: PRT
<213> ORGANISM: Artificial Sequence
<220> FEATURE:
<223> OTHER INFORMATION: antibody

<400> SEQUENCE: 64

Glu Val Gln Leu Val Gln Ser Gly Pro Glu Val Lys Lys Pro Gly Glu
  1               5                  10                  15

Ser Leu Arg Ile Ser Cys Lys Gly Ser Gly Tyr Val Phe Thr Ser Tyr
                 20                  25                  30

Trp Leu His Trp Val Arg Gln Ala Pro Gly Gln Gly Leu Glu Trp Met
             35                  40                  45

Gly Tyr Ile Asn Pro Arg Asn Asp Tyr Thr Glu Tyr Asn Arg Ile Phe
     50                  55                  60

Lys Gly Arg Val Thr Ile Ser Ala Asp Lys Ser Ile Asn Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Arg Gly Ile Thr Thr Phe Tyr Trp Gly Gln Gly
            100                 105
```

ANTI-CD22 ANTIBODIES

BACKGROUND OF THE INVENTION

1. Field of the Invention

The present invention relates to antibodies, including specified portions or variants, specific for at least one CD22 protein or fragment thereof, as well as nucleic acids encoding such anti-CD22 antibodies, complementary nucleic acids, vectors, host cells, and methods of making and using thereof, including therapeutic formulations, administration and devices.

2. Related Art

CD22 is a member of the Siglec, sialic acid binding receptor protein superfamily, and is produced by developing B cells. In vivo, B cells represent the main sources of CD22. Other cells such as lymphoma, leukemic and lymphocytic B cells also produce CD22. CD22 has been implicated as a prognostic factor for non-Hodgkin's lymphoma and both acute and chronic lymphocytic leukemias cancer progression. CD22 production can be regulated by B-cell differentiation processes in the germinal centers of lymph nodes.

CD22 ligands, sialic-acid containing extracellular surface molecules, can bind to the CD22 receptor expressed on developing B cells during the humoral immune responses. The CD22 receptor has immunoglobin-like repeat sequences that are responsible for CD22-ligand binding.

There are at least two major biological functions of CD22: CD22 can interact with the B cell receptor complex (BCR) to stimulate cellular signaling to promote B cell differentiation and production of immunoglobulins, and can also interact with the BCR to inhibit cellular signaling and cell growth and differentiation. Binding of the murine monoclonal anti-CD22 antibody stimulates CD22 tyrosine phosphorylation and negatively regulates mitogenic signal transduction (Carnahan et al., Cancer Res Sep. 1, 2003 9; 3982s)

There is a need to provide high affinity, neutralizing chimeric or human antibodies to CD22 or fragments thereof for use in preventing, treating, ameliorating, or diagnosing conditions related to lymphoma, acute and chronic leukemias and other B-cell dysplasias and B-cell dependent autoimmune diseases.

SUMMARY OF THE INVENTION

The present invention provides isolated humanized, anti-CD22 antibodies, having at least one antigen binding region derived from the high affinity VM1000, VM1001, VM1002, VM1003, VM1004, VM1005, VM1006, VM1007, VM1008, VM1009, VM1010, VM1011, VM1012, VM1013, VM1014, or VM1015 anti-CD22 antibodies, as well as anti-CD22 antibody compositions, conjugated version of these anti-CD22 antibodies, encoding or complementary nucleic acids, vectors, host cells, compositions, formulations, devices, transgenic animals, transgenic plants related thereto, and methods of making and using thereof, as described and enabled herein, in combination with what is known in the art. The antibodies of the invention specifically neutralize human CD22 with high affinity.

The present invention provides at least one isolated anti-CD22 antibody as described herein. The antibody according to the present invention includes any one of VM1000, VM1001, VM1002, VM1003, VM1004, VM1005, VM1006, VM1007, VM1008, VM1009, VM1010, VM1011, VM1012, VM1013, VM1014, or VM1015, or any protein or peptide molecule that comprises at least one complementarity determining region (CDR) (e.g., CDR1, CDR2 or CDR3) of a heavy or light chain or a ligand binding portion thereof, derived from one of VM1000, VM1001, VM1002, VM1003, VM1004, VM1005, VM1006, VM1007, VM1008, VM1009, VM1010, VM1011, VM1012, VM1013, VM1014, or VM1015, in combination with a heavy chain or light chain constant region, a framework region, or any portion thereof, that can be incorporated into an antibody of the present invention. In one embodiment the invention is directed to an anti-CD22 antibody comprising a light chain and a heavy chain, each of the chains comprising at least part of a human constant region and at least part of a variable region (v) derived from one or more of VM1000, VM1001, VM1002, VM1003, VM1004, VM1005, VM1006, VM1007, VM1008, VM1009, VM1010, VM1011, VM1012, VM1013, VM1014, or VM1015 each of which has specificity to human CD22, said antibody binding with high affinity to an inhibiting and/or neutralizing epitope of human CD22. The invention also includes fragments or a derivative of such an antibody, such as one or more portions of the antibody chain, such as the heavy chain constant, joining, diversity or variable regions, or the light chain constant, joining or variable regions.

The antibody can comprise at least one specified portion of at least one complementarily determining region (CDR) (e.g., CDR1, CDR2 or CDR3 of the heavy or light chain variable region) derived from an anti-CD22 antibody (as such term is defined herein), and/or at least one constant or variable framework region or any portion thereof. The antibody amino acid sequence can further optionally comprise at least one specified substitution, insertion or deletion as described herein or as known in the art.

Preferred antibodies of the present invention include VM1000, VM1001, VM1002, VM1003, VM1004, VM1005, VM1006, VM1007, VM1008, VM1009, VM1010, VM1011, VM1012, VM1013, VM1014, and VM1015, as well as fragments and regions thereof.

In one embodiment, the disclosure provides an isolated antibody or antibody fragment that binds to human CD22, comprising a heavy chain variable region having the amino acid sequence of SEQ ID NO: 49, 50, 51, 52, 53, 54, 55, 56, 57, 58, 59, 60, 61, 62, 63, or 64; a light chain variable region having the amino acid sequence of SEQ ID NO: 17, 18, 19, 20, 21, 22, 23, 24, 25, 26, 27, 28, 29, 30, 31 or 32; and a constant region derived from one or more human antibodies. In one aspect, the disclosure provides an isolated antibody or antibody fragment that binds to human CD22, comprising a heavy chain and light chain complementarity determining regions (CDRs) derived from the variable regions from one or more of VM1000, VM1001, VM1002, VM1003, VM1004, VM1005, VM1006, VM1007, VM1008, VM1009, VM1010, VM1011, VM1012, VM1013, VM1014, and VM1015, and a constant region derived from one or more human antibodies. In another aspect, the disclosure provides an antibody or fragment according to claim 1 or 2, wherein said antibody or fragment competitively inhibits in vivo the binding to human CD22 of an anti CD22 murine antibody.

Preferred antibodies of the present invention are those that bind human CD22 and induce CD22 tyrosine phosphorylation and internalization and negatively regulate B4 cell growth and differentiation. Preferred methods for determining monoclonal antibody specificity and affinity by competitive inhibition can be found in Harlow, et al, Antibodies: A Laboratory Manual, Cold Spring Harbor Laboratory Press, Cold Spring Harbor, N.Y., 1988), hereby incorporated by reference into the present application. At least one antibody of the invention binds at least one specified epitope specific to human CD22 protein, subunit, fragment, portion or any combination thereof, for example as described by (Stein R, Belisle E, Hansen H J, Goldenberg D M: Epitope specificity of the anti-(B cell lymphoma) monoclonal antibody, LL2. *Cancer Immunol Immunother* 1993, 37:293-298.) The monoclonal antibody LL2 binds to the third immunoglobulin (Ig) repeat sequence in the extracellular domain of CD22 and is important for its modulatory effects on CD22 expressing B cell populations and lymphoma and leukemia cells. The epitope can comprise at least one antibody binding region, which epitope is preferably comprised of at least 1-5 amino acids of at least one portion thereof, such as but not limited to, at least one functional, extracellular, soluble, hydrophillic, external or cytoplasmic domain of human CD22 protein, or any portion thereof.

In one aspect, the present invention provides at least one isolated mammalian anti-CD22 antibody, comprising at least one variable region from one of VM1000, VM1001, VM1002, VM1003, VM1004, VM1005, VM1006, VM1007, VM1008, VM1009, VM1010, VM1011, VM1012, VM1013, VM1014, and VM1015 and the nucleic acid sequences encoding them.

In another aspect, the present invention provides at least one isolated mammalian anti-CD22 antibody, comprising either (i) all of the heavy chain complementarity determining regions (CDR) amino acid sequences derived from VM1000, VM1001, VM1002, VM1003, VM1004, VM1005, VM1006, VM1007, VM1008, VM1009, VM1010, VM1011, VM1012, VM1013, VM1014, or VM1015 and the nucleic acid sequences encoding them; or (ii) all of the light chain CDR amino acids sequences from one of VM1000, VM1001, VM1002, VM1003, VM1004, VM1005, VM1006, VM1007, VM1008, VM1009, VM1010, VM1011, VM1012, VM1013, VM1014, or VM1015 and the nucleic acid sequences encoding them.

In another aspect, the present invention provides at least one isolated mammalian anti-CD22 antibody, comprising at least one heavy chain or light chain CDR having the amino acid sequence derived from VM1000, VM1001, VM1002, VM1003, VM1004, VM1005, VM1006, VM1007, VM1008, VM1009, VM1010, VM1011, VM1012, VM1013, VM1014, and VM1015 and the nucleic acid sequences encoding them.

In other aspect the present invention provides at least one isolated mammalian chimeric, humanized or CDR-grafted anti-CD22 antibody, comprising at least one human CDR, or no human CDRs, wherein the antibody specifically binds at least one epitope comprising at least 1-3 amino acids of an epitope of human CD22.

At least one antibody can optionally further bind CD22 with an affinity ($K_D$ of at least $10^{-9}$ M, preferably at least $10^{-10}$ M, and/or substantially neutralize at least one activity of at least one CD22 protein. In a preferred embodiment, the antibody binds CD22 with an affinity ($K_{Ds}$) of at least $5 \times 10^{-10}$ M, preferably $5 \times 10^{-11}$, more preferably $5 \times 10^{-12}$ and neutralizes human CD22.

The present invention provides, in one aspect, isolated nucleic acid molecules comprising, complementary, or hybridizing to, a polynucleotide encoding the aforementioned specific anti-CD22 antibodies, comprising at least one specified sequence, domain, portion or variant thereof. The present invention further provides recombinant vectors comprising said anti-CD22 antibody nucleic acid molecules, host cells containing such nucleic acids and/or recombinant vectors, as well as methods of making and/or using such antibody nucleic acids, vectors and/or host cells. Thus, the invention comprises isolated nucleic acid encoding at least one isolated mammalian anti-CD22 antibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof. Also provided is a method for producing at least one anti-CD22 antibody, comprising translating the antibody encoding nucleic acid under conditions in vitro, in vivo or in situ, such that the CD22 antibody is expressed in detectable or recoverable amounts.

The present invention also provides at least one method for expressing at least one aforementioned anti-CD22 antibody, in a host cell, comprising culturing a host cell as described herein under conditions wherein at least one anti-CD22 antibody is expressed in detectable and/or recoverable amounts.

The present invention also provides at least one composition comprising (a) an isolated anti-CD22 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-CD22 antibody method or composition, for administering a therapeutically effective amount to modulate or treat at least one CD22 related condition in a cell, tissue, organ, animal or patient and/or, prior to, subsequent to, or during a related condition, as known in the art and/or as described herein. Thus, the invention provides a method for diagnosing or treating a CD22 related condition in a cell, tissue, organ or animal, comprising contacting or administering a composition comprising an effective amount of at least one isolated anti-CD22 antibody of the invention with, or to, the cell, tissue, organ or animal. The method can optionally further comprise using an effective amount of 0.001-50 mg/kilogram of an anti-CD22 antibody of the invention to the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, a cytokine antagonist, and an anti-TNFα or other monoclonal antibody or bifunctional antibody.

The present invention further provides at least one anti-CD22 antibody method for diagnosing at least one CD22 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-CD22 antibody, according to the present invention.

Also provided is a medical device, comprising at least one isolated mammalian anti-CD22 antibody of the invention, wherein the device is suitable to contacting or administering the at least one anti-CD22 antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one anti-CD22 antibody or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of anti-CD22 antibody or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. In one aspect, the disclosure provides a method of treating at least one CD22 mediated condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one isolated mammalian anti-CD22 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides any invention described herein.

DESCRIPTION OF THE FIGURES

FIG. 1 shows the nucleic acid sequences and amino acid sequences, respectively, for the light chain (SEQ ID NOs: 1, 17) and heavy chain (SEQ ID NOs: 33, 49) variable region of VM1000.

FIG. 2 shows the nucleic acid sequences and amino acid sequences, respectively, for the light chain (SEQ ID NOs: 2, 18) and heavy chain (SEQ ID NOs: 34, 50) variable region of VM1001.

FIG. 3 shows the nucleic acid sequences and amino acid sequences, respectively, for the light chain (SEQ ID NOs: 3, 19) and heavy chain (SEQ ID NOs: 35, 51) variable region of VM1002.

FIG. 4 shows the nucleic acid sequences and amino acid sequences, respectively, for the light chain (SEQ ID NOs: 4, 20) and heavy chain (SEQ ID NOs: 36, 52) variable region of VM1003.

FIG. 5 shows the nucleic acid sequences and amino acid sequences, respectively, for the light chain (SEQ ID NOs: 5, 21) and heavy chain (SEQ ID NOs: 37, 53) variable region of VM1004.

FIG. 6 shows the nucleic acid sequences and amino acid sequences, respectively, for the light chain (SEQ ID NOs: 6, 22) and heavy chain (SEQ ID NOs: 38, 54) variable region of VM1005.

FIG. 7 shows the nucleic acid sequences and amino acid sequences, respectively, for the light chain (SEQ ID NOs: 7, 23) and heavy chain (SEQ ID NOs: 39, 55) variable region of VM1006.

FIG. 8 shows the nucleic acid sequences and amino acid sequences, respectively, for the light chain (SEQ ID NOs: 8, 24) and heavy chain (SEQ ID NOs: 40, 56) variable region of VM1007.

FIG. 9 shows the nucleic acid sequences and amino acid sequences, respectively, for the light chain (SEQ ID NOs: 9, 25) and heavy chain (SEQ ID NOs: 41, 57) variable region of Anti-CD22 Ab VM1008.

FIG. 10 shows the nucleic acid sequences and amino acid sequences, respectively, for the light chain (SEQ ID NOs: 10, 26) and heavy chain (SEQ ID NOs: 42, 58) variable region of VM1009.

FIG. 11 shows the nucleic acid sequences and amino acid sequences, respectively, for the light chain (SEQ ID NOs: 11, 27) and heavy chain (SEQ ID NOs: 43, 59) variable region of VM1010.

FIG. 12 shows the nucleic acid sequences and amino acid sequences, respectively, for the light chain (SEQ ID NOs: 12, 28) and heavy chain (SEQ ID NOs: 44, 60) variable region of VM1011.

FIG. 13 shows the nucleic acid sequences and amino acid sequences, respectively, for the light chain (SEQ ID NOs: 13, 29) and heavy chain (SEQ ID NOs: 45, 61) variable region of VM1012.

FIG. 14 shows the nucleic acid sequences and amino acid sequences, respectively, for the light chain (SEQ ID NOs: 14, 30) and heavy chain (SEQ ID NOs: 46, 62) variable region of VM1013.

FIG. 15 shows the nucleic acid sequences and amino acid sequences, respectively, for the light chain (SEQ ID NOs: 15, 31) and heavy chain (SEQ ID NOs: 47, 63) variable region of VM1014.

FIG. 16 shows the nucleic acid sequences and amino acid sequences, respectively, for the light chain (SEQ ID NOs: 16, 32) and heavy chain (SEQ ID NOs: 48, 64) variable region of VM1015.

FIG. 17 shows data for the affinity ELISA analysis of selected clones of VM1000, VM1001, VM1002, VM1003, VM1004, VM1005, VM1006, VM1007, VM1008, VM1009, VM1010, VM1011, VM1012, VM1013, VM1014, and VM1015 of the invention.

FIG. 18 shows data for the Surface Plasmon Resonance (SPR) determination of the affinity constants (KD) for recombinant CD22 extracellular domain of VM1000, VM1001, VM1002, VM1003, VM1004, VM1005, VM1006, VM1007, VM1008, VM1009, VM1010, VM1011, VM1012, VM1013, VM1014, and VM1015 of the invention and controls (VM006G and VM006H).

FIG. 20 shows a table with data from surface binding and internalization analysis using FACS of VM1000, VM1001, VM1002, VM1003, VM1004, VM1005, VM1006, VM1007, VM1008, VM1009, VM1010, VM1011, VM1012, VM1013, VM1014, and VM1015 and a control (BA006G).

FIG. 21 shows data for the rapid surface binding and intracellular internalization using quantitative confocal immunofluorescent microscopy of antibodies VM1000, VM1001, VM1002, VM1003, VM1004, VM1005, VM1006, VM1007, VM1008, VM1009, VM1010, VM1011, VM1012, VM1013, VM1014, and VM1015 of the invention.

FIG. 24 shows high level expression data in mammalian cells of anti-CD22 antibodies of the present invention.

DETAILED DESCRIPTION OF THE INVENTION

Citations

Figure 19:
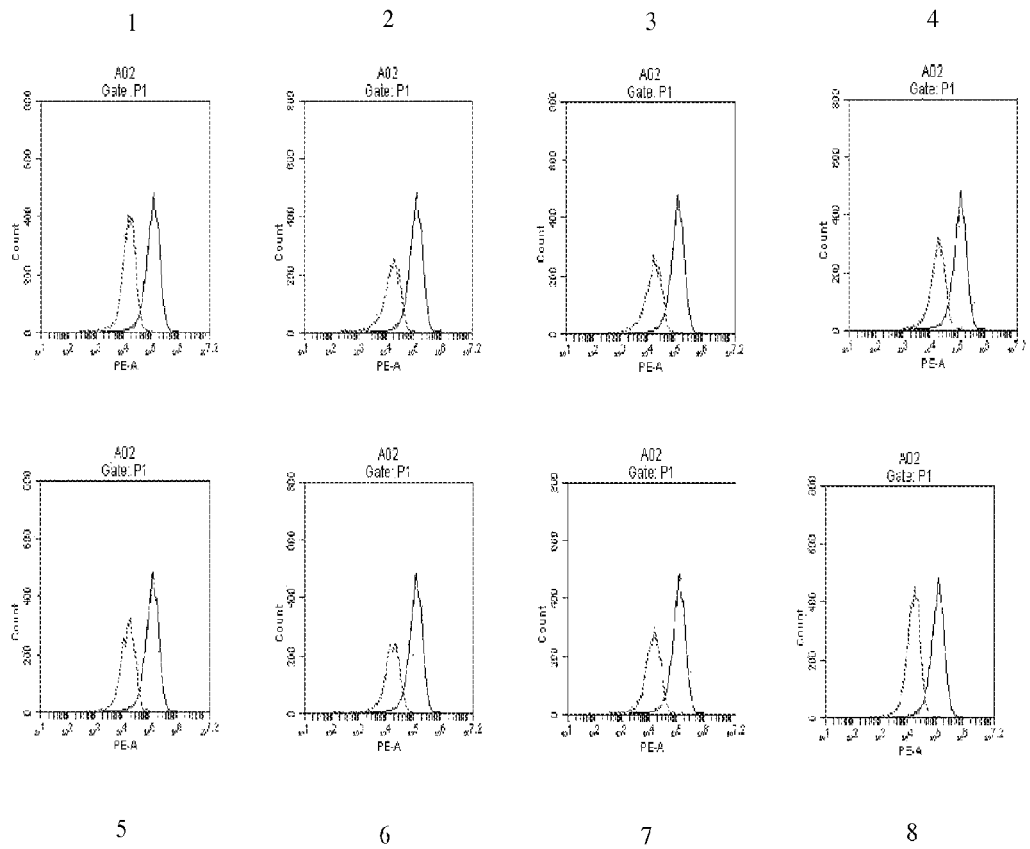
FIG. 19 shows data for the surface binding and internalization analysis on CD22 expressing human lymphoma cells, such as Daudi, RAMOS and RAJI B cell lines by fluorescent activated cell sorting (FACS) of selected clones from VM1000, VM1001, VM1002, VM1003, VM1004, VM1005, VM1006, VM1007, VM1008, VM1009, VM1010, VM1011, VM1012, VM1013, VM1014, and VM1015 as well as controls. All peaks on the right in each Box represent the control (no antibody); all peaks on the left in each Box show data with antibody, whereby shifts to lower fluorescent signal indicate receptor/antibody internalization. Box 1 shows a positive control antibody, Box 2 shows VM1000, Box 3 shows VM1001, Box 4 shows VM1002, Box 5 shows VM1004, Box 6 shows VM1005, Box 7 shows VM1006, and Box 8 shows VM1011.

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino Acid Codes

The amino acids that make up anti-CD22 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994).

Definitions

As used herein, an "Anti-CD22 antibody," "Anti-CD22 antibody," "Anti-CD22 antibody portion," or "Anti-CD22 antibody fragment" and/or "Anti-CD22 antibody variant" and the like include any protein or peptide containing molecule that comprises at least a portion of an immunoglobulin molecule, containing at least one complementarity determining region (CDR) of a heavy or light chain or a ligand binding portion thereof derived from at least one of VM1000, VM1001, VM1002, VM1003, VM1004, VM1005, VM1006, VM1007, VM1008, VM1009, VM1010, VM1011, VM1012, VM1013, VM1014, or VM1015, in combination with a heavy chain or light chain variable region, a heavy chain or light chain constant region, a framework region, or any portion thereof, of non-murine origin, preferably of human origin, which can be incorporated into an antibody of the present invention. Alternatively, the term "Anti-CD22 antibody" shall refer collectively or individually to the humanized monoclonal antibodies VM1000, VM1001, VM1002, VM1003, VM1004, VM1005, VM1006, VM1007, VM1008, VM1009, VM1010, VM1011, VM1012, VM1013, VM1014, and VM1015. Such antibody is capable of modulating, decreasing, antagonizes, mitigates, alleviates, blocks, inhibits, abrogates and/or interferes with at least one CD22 activity or binding, or with CD22 receptor activity or binding, in vitro, in situ and/or in vivo. As a non-limiting example, a suitable Anti-CD22 antibody, specified portion or variant of the present invention can bind with high affinity to an inhibiting and/or neutralizing epitope of human CD22 recognized by at least one of VM1000, VM1001, VM1002, VM1003, VM1004, VM1005, VM1006, VM1007, VM1008, VM1009, VM1010, VM1011, VM1012, VM1013, VM1014, or VM1015 monoclonal antibody. A suitable Anti-CD22 antibody, specified portion, or variant can also optionally affect at least one of CD22 activity or function, such as but not limited to, RNA, DNA or protein synthesis, CD22 release, CD22 receptor signaling, membrane CD22 cleavage, CD22 activity, CD22 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof, each containing at least one CDR derived from an Anti-CD22. Functional fragments include antigen-binding fragments that bind to a mammalian CD22. For example, antibody fragments capable of binding to CD22 or portions thereof, including, but not limited to Fab' (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

As used herein "chimeric" antibodies or "humanized" antibodies or "CDR-grafted" include any combination of the herein described Anti-CD22 Abs, or any CDR derived therefrom combined with one or more proteins or peptides derived from a non-murine, preferably, human antibody. In accordance with the invention, chimeric or humanized antibodies include those wherein the CDR's are derived from one or more of the Anti-CD22 Abs described herein and at least a portion, or the remainder of the antibody is derived from one or more human antibodies. Thus, the human part of the antibody may include the framework, $C_L$, $C_H$ domains (e.g., $C_{H1}$, $C_{H2}$, $C_{H3}$), hinge, ($V_L$, $V_H$)) regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDR's while simultaneously maximizing the humanization of the antibody. Such changes or variations optionally and preferably retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

For full-length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

Several publications describe in detail uses, applications and methods of use and application of anti-CD22 antibodies, including anti-CD22 antibodies of the present invention, for example U.S. Patent Application Number US20110182887 entitled "Humanized Anti-CD22 Antibodies and Their Use", U.S. Patent Application Number US20110020344 entitled "Human Monoclonal Antibodies Specific for CD22", and U.S. Patent Application Number US20100143368 entitled "Human Antibodies That Bind CD22 and Uses Thereof" all of which are incorporated herein by reference.

Antibodies of the Present Invention

In accordance with the present invention, the Anti-CD22 antibodies comprise any one of VM1000, VM1001, VM1002, VM1003, VM1004, VM1005, VM1006, VM1007, VM1008, VM1009, VM1010, VM1011, VM1012, VM1013, VM1014, or VM1015 antibodies or an antibody in which the variable region or CDRs are derived from any one of VM1000, VM1001, VM1002, VM1003, VM1004, VM1005, VM1006, VM1007, VM1008, VM1009, VM1010, VM1011, VM1012, VM1013, VM1014, or VM1015 antibody and the framework and constant regions of the antibody are derived from one or more human antibodies. The variable region or CDRs derived from the antibody preferably have from about 90% to about 100% identity with the variable region or CDRs of any one of VM1000, VM1001, VM1002, VM1003, VM1004, VM1005, VM1006, VM1007, VM1008, VM1009, VM1010, VM1011, VM1012, VM1013, VM1014, or VM1015 antibody, although any and all modifications, including substitutions, insertions and deletions, are contemplated so long as the chimeric antibody maintains the ability to bind to and inhibit CD22. The regions of the chimeric, humanized or CDR-grafted antibodies that are derived from human antibodies need not have 100% identity with the human antibodies. In a preferred embodiment, as many of the human amino acid residues as possible are retained in order that immunogenicity is negligible, but the human residues, in particular residues of the framework region, are substituted as required and as taught herein below in accordance with the present invention. Such modifications as disclosed herein are necessary to support the antigen binding site formed by the CDRs while simultaneously maximizing the humanization of the antibody.

In accordance with the present invention, the nucleic acid sequences and the deduced amino acid sequences of the variable regions (light and heavy chain) of the Anti-CD22 antibodies are set forth in FIGS. 1-15. Each of the heavy and light chain variable regions contain three CDRs that combine to form the antigen binding site. The three CDRs are surrounded by four framework regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4$^{th}$ ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

In a preferred embodiment the CDRs are derived from any one of VM1000, VM1001, VM1002, VM1003, VM1004, VM1005, VM1006, VM1007, VM1008, VM1009, VM1010, VM1011, VM1012, VM1013, VM1014, or VM1015. Determination of the heavy chain CDRs and light chain CDRs is well within the skill of one in the art. See, for example, http://www.bioinf.org.uk/abs/.

The sequences of the CDRs of the Anti-CD22 antibody may be modified by insertions, substitutions and deletions to the extent that the CDR-grafted antibody maintains the ability to bind to and inhibit human CD22. The ordinarily skilled artisan can ascertain the maintenance of this activity by performing the functional assays described herein below.

Alternatively, the entire heavy chain variable region and light chain variable region of any one of VM1000, VM1001, VM1002, VM1003, VM1004, VM1005, VM1006, VM1007, VM1008, VM1009, VM1010, VM1011, VM1012, VM1013, VM1014, or VM1015 may be combined with the human constant and framework regions to form the chimeric antibody of the present invention. Clone VM1000 comprises light chain VM1000LC (SEQ ID NO: 1) and heavy chain VM1000HC (SEQ ID NO: 33). Clone VM1001 comprises light chain VM1001LC (SEQ ID NO: 2) and heavy chain VM1001HC (SEQ ID NO: 34). Clone VM1002 comprises light chain VM1002LC (SEQ ID NO: 3) and heavy chain VM1002HC (SEQ ID NO: 35). Clone VM1003 comprises light chain VM1003LC (SEQ ID NO: 4) and heavy chain VM1003HC (SEQ ID NO: 36). Clone VM1004 comprises light chain VM1004LC (SEQ ID NO: 5) and heavy chain VM1004HC (SEQ ID NO: 37). Clone VM1005 comprises light chain VM1005LC (SEQ ID NO: 6) and heavy chain VM1005HC (SEQ ID NO: 38). Clone VM1006 comprises light chain VM1006LC (SEQ ID NO: 7) and heavy chain VM1006HC (SEQ ID NO: 39). Clone VM1007 comprises light chain VM1007LC (SEQ ID NO: 8) and heavy chain VM1007HC (SEQ ID NO: 40). Clone VM1008 comprises light chain VM1008LC (SEQ ID NO: 9) and heavy chain VM1008HC (SEQ ID NO: 41). Clone VM1009 comprises light chain VM1009LC (SEQ ID NO: 10) and heavy chain VM1009HC (SEQ ID NO: 42). Clone VM1010 comprises light chain VM1010LC (SEQ ID NO: 11) and heavy chain VM1010HC (SEQ ID NO: 43). Clone VM1011 comprises light chain VM1011LC (SEQ ID NO: 12) and heavy chain VM1011HC (SEQ ID NO: 44). Clone VM1012 comprises light chain VM1012LC (SEQ ID NO: 13) and heavy chain VM1012HC (SEQ ID NO: 45). Clone VM1013 comprises light chain VM1013LC (SEQ ID NO: 14) and heavy chain VM1013HC (SEQ ID NO: 46). Clone VM1014 comprises light chain VM1014LC (SEQ ID NO: 15) and heavy chain VM1014HC (SEQ ID NO: 47). Clone VM1015 comprises light chain VM1015LC (SEQ ID NO: 16) and heavy chain VM1015HC (SEQ ID NO: 48).

Human genes which encode the constant (C) regions of the humanized antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including y, p, a, 5, E, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1).

The human $C_L$ region can be derived from either human L chain isotype, kappa or lambda, preferably kappa.

Genes encoding human immunoglobulin C regions are obtained from human cells by standard cloning techniques (Sambrook, et al. (Molecular Cloning: A Laboratory Manual, 2$^{nd}$ Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof. Chimeric antibody fragments, such as F(ab$^1$)$_2$ and Fab, can be prepared by designing a chimeric H chain gene which is appropriately truncated. For example, a chimeric gene encoding an H chain portion of an F(ab$^1$)$_2$ fragment would include DNA sequences encoding the CH1 domain and hinge region of the H chain, followed by a translational stop codon to yield the truncated molecule.

Generally, in one example, humanized antibodies, fragments and regions of the present invention are produced by cloning DNA segments encoding the H and L chain antigen-binding regions of the Anti CD22 specific antibody, and joining these DNA segments to DNA segments including $C_H$ and $C_L$ regions, respectively, to produce full length immunoglobulin-encoding genes.

The sequences of the variable regions of the antibody may be modified by insertions, substitutions and deletions to the extent that the chimeric antibody maintains the ability to bind to and inhibit human CD22. The ordinarily skilled artisan can ascertain the maintenance of this activity by performing the functional assays described hereinbelow. The variable regions can have, for example, from about 50% to about 100% homology to the variable regions of SEQ ID NOS: 1-64. In a preferred embodiment, the variable regions of the antibody have from about 80% to about 100% homology to the variable regions of SEQ ID NOS: 1-64. In a more preferred embodiment the variable regions have from about 90% to about 100% homology to the variable regions of SEQ ID NOS: 1-64.

In one specific aspect, preferred anti-CD22 Mabs of the disclosure comprise variable light chain regions having 95%, 96%, 97%, 98% or 99% amino acid sequence homology to SEQ ID NO: 17-32 and further comprise variable heavy chain regions having 95%, 96%, 97%, 98% or 99% amino acid sequence homology to SEQ ID NO: 49-64.

In one specific aspect, preferred anti-CD22 Mabs of the disclosure comprise a variable light chain region selected from one of SEQ ID NO: 1-16. In another specific aspect, preferred anti-CD22 Mabs of the disclosure comprise a variable heavy chain region selected from one of SEQ ID NO: 33-48.

Methods for engineering or humanizing non-human or human antibodies can be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcani.com/; www.antibodyresource.com/onlinecomp.html; www.public.iastate.edu/.about/pedro/research_tools.html; www.mgen.uni-heidelberg.de/SD/IT/IT.html; www.whfreeman.comimmunology/CH05/kuby05.htm; www.library.thinkquesL.org/12429/Immune/Antibody.html; www.hhmi.org/grants/lectures/1996/vlab/; www.path.canl.ac.uk/.about.mrc7/mikeimages.html; www.antibodyresource.com/; mcb.harvard.edu/BioLinks/Immunology.html. www.immunologylink.com/; pathbox.wustl.edu/.about.hcenter/index.html; www.biotech.ufl.edu-.about.hcl/; www.pebio.com/pa/340913/340913.html; www.nal.usda.gov/awic/pubs/antibody/; www.m.ehime-u.ac.jp/.about.yasuhito/Elisa.html; www.biodesign.com/table.asp; www.icnet.uk/axp/facs/davies/links.html; www.biotech.ufl.edu/.about.fccl/protocol.html; www.isac-neL.org/sites_geo.html; aximtl.imt.uni-marburg.de/.abouL.rek/AEPStart.html; bserv.uci.kun.nhl.abouLjraats/links1.html; www.recab.uni-hd.de/immuno.bme.nwvu.edu/; www.mrc-cpe.cani.ac.uk/imt-doc/public/INTRO.html; www.ibt.unani.mx/vir/V_mice.html; imgt.cnusc.fr:8104/; www.biochem.ucl.ac.uk/.about.martin/abs/index.html; antibody.bath.ac.uk/; abgen.cvm.tamiu.edullab/wwwabgen.html; www.unizh.ch/.about.honegger/AHOsenminar/Slide01.htnml; www.cryst.bbk.ac.uk/.about.ubcg07s/; www.nimr.mrc.ac.uk/CC/ccaewg/ccaewg.htm; www.path-.cam.ac.uk.about.mrc7/humanisationTAHHP.html; www.ibt.unun.mx/vir/structure/stat_aim.html; www.biosci.missouri.edu/smithgp/index.html; www.cryst.bioc.cani.ac.uk/.about.fmolina/Web-pages/Pept/spottech.html; www.jeiini.de/fr_products.html; www.patents.ibm.con/ibm-.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The human constant region of the humanized antibody of the invention can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the anti-human CD22 human antibody comprises an IgG1 heavy chain and a IgG1 K light chain. The isolated anti-CD22 antibodies of the present invention comprise antibody amino acid sequences disclosed herein encoded by any suitable polynucleotide as well as. Preferably, the antibody or antigen-binding fragment binds human CD22 and, thereby partially or substantially neutralizes at least one biological activity of the protein. The antibody, or specified portion or variant thereof, partially or preferably substantially neutralizes at least one biological activity of at least one CD22 protein or fragment and thereby inhibit activities mediated through the binding of CD22 to the CD22 receptor or through other CD22-dependent or mediated mechanisms. As used herein, the term "neutralizing antibody" refers to an antibody that can inhibit an CD22-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an Anti-CD22 antibody to inhibit a CD22-dependent activity is preferably assessed by at least one suitable CD22 protein or receptor assay, as described herein and/or as known in the art.

At least one antibody of the invention binds at least one specified epitope specific to at least one CD22 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR4, CDR5 and CDR6) or variant of at least one light chain variable region, derived from an anti-CD22 Ab described herein. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the antibody or antigen-binding portion or variant can have an antigen-binding region that comprises at least a portion of at least one light chain CDR (i.e., CDR4, CDR5 and/or CDR6) having the amino acid sequence of the corresponding CDRs 4, 5 and/or 6. In a preferred embodiment the three heavy chain CDRs and the three light chain CDRs of the antibody or antigen-binding fragment have the amino acid sequence of the corresponding CDR of at least one of VM1000, VM1001, VM1002, VM1003, VM1004, VM1005, VM1006, VM1007, VM1008, VM1009, VM1010, VM1011, VM1012, VM1013, VM1014, or VM1015. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method and using any of the possible redundant codons that will result in expression of a polypeptide of the invention.

Liquid phase synthesis of combinatorial variable domain humanized libraries for the light chain and the heavy chain can be employed. The assembly of a humanized light chain (LC) variable domain library, for example, contains human light chain frameworks (FW) and non-human complementarity determining regions (CDR). The library is assembled by, for example, by using stepwise liquid phase ligation of FW and CDR DNA fragments. The libraries are assembled by using stepwise liquid phase ligation of FW and CDR DNA fragments in the order of FW1-CDR1-FW2-CDR2-FW3-CDR3 by techniques known to one of skill in the art. For example, by the techniques of one or more of the following references, each of which is incorporated herein by reference. Lo, B. K., 2003, Antibody humanization by CDR grafting. Antibody Engineering, Methods and protocols. Edit by Benny K. C. Lo, Methods in Molecular Biology, 248, 135-159; Kashmiri et al., 2003, Developing a minimally immunogenic humanized antibody by CDR grafting. Antibody Engineering, Methods and protocols. Edit by Benny K. C. Lo, Methods in Molecular Biology, 248, 361-376; Bassette, P. H., et al., 2003, Construction of Designed Protein Libraries Using Gene Assembly Mutagenesis. Directed Evolution Library Creation, Methods and protocols. Edit. Arnold and Georgiou, Methods in Molecular Biology, 231, 29-37; Chames, P., et al., 2001, Selections on Biotinylated antigens. Antibody Engineering, Edit by R. Kontermann and S. Dubel, Springer Lab Manual, 149-166; O'Brien S., and Jones, T., 2001, Humanising antibodies by CDR grafting. Antibody Engineering, Edit by R. Kontermann and S. Dubel, Springer Lab Manual, 567-590.

Antibodies that bind to human CD22 and that comprise the defined heavy or light chain variable region or CDR regions can be prepared using suitable methods, such as phage display (Katsube, Y., et al., Int J. Mol. Med, 1(5): 863-868 (1998)) or methods that employ transgenic animals, as known in the art and/or as described herein. For example, the antibody, specified portion or variant can be expressed using the encoding nucleic acid or portion thereof in a suitable host cell.

As stated, the invention also relates to antibodies, antigen-binding fragments, immunoglobulin chains and CDRs comprising amino acids in a sequence that is substantially the same as an amino acid sequence described herein. Such Anti-CD22 antibodies can include one or more amino acid substitutions, deletions or additions, either from natural mutations or human manipulation, as specified herein. Preferably, such antibodies or antigen-binding fragments and antibodies comprising such chains or CDRs can bind human CD22 with high affinity (e.g., $K_D$ less than or equal to about $10_{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given Anti-CD22 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an Anti-CD22 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one CD22 neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-CD22 antibodies of the present invention can include, but are not limited to, at least one portion, sequence or combination selected from 5 to all of the contiguous amino acids of at least one of CDRs derived from SEQ ID NOS: 17-32 and 49-64.

An Anti-CD22 antibody can further optionally comprise a polypeptide of at least one of 70-100% of the contiguous amino acids of the CDRs derived from at least one of SEQ ID NOS: 17-32 and 49-64. In one specific aspect, the anti-CD22 antibody comprises a polypeptide of 95-99% sequence homology to SEQ ID NO: 1-16. In another specific aspect, the anti-CD22 antibody comprises a polypeptide of 95-99% sequence homology to SEQ ID NO: 33-48.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of at least one of SEQ ID NOS: 17-32 or 49-64. Preferably, 70-100% amino acid identity (i.e., 90, 91, 92, 93, 94, 95, 96, 97, 98, 99, 100 or any range or value therein) is determined using a suitable computer algorithm, as known in the art. In one specific aspect, the anti-CD22 antibody comprises a polypeptide of 95-99% sequence homology to SEQ ID NO: 17-32 or 49-64.

Exemplary heavy chain and light chain variable regions sequences are provided in SEQ ID NOS: 1-64. The antibodies of the present invention, or specified variants thereof, can comprise any number of contiguous amino acid residues from an antibody of the present invention, wherein that number is selected from the group of integers consisting of from 10-100% of the number of contiguous residues in an Anti-CD22 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-δ 9-octadecanoate ($C_{18}$, oleate), all cis-δ 5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The antibodies of the invention can bind human CD22 with a wide range of affinities ($K_D$). In a preferred embodiment at least one human mAb of the present invention can optionally bind human CD22 with high affinity. For example, a mAb can bind human CD22 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Anti-CD22 antibodies useful in the methods and compositions of the present invention are characterized by high affinity binding to CD22 and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:1125-1127 (1994), entirely incorporated herein by reference).

Bispecific, heterospecific, heteroconjugate or similar antibodies can also be used that are monoclonal, humanized, antibodies that have binding specificities for at least two different antigens. In the present case, one of the binding specificities is for at least one CD22 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Nucleic Acid Molecules

Using the information provided herein, such as the nucleotide sequences encoding at least 70-100% of the contiguous amino acids of at least one of SEQ ID NOS: 17-32 or 49-64, variants or consensus sequences thereof, or a deposited vector comprising at least one of these sequences, a nucleic acid molecule of the present invention encoding at least one Anti-CD22 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS: 33-48) or light chain (e.g., SEQ ID NOS: 1-16); nucleic acid molecules comprising the coding sequence for an anti-CD22 antibody or variable region; and nucleic acid molecules which comprise a nucleotide sequence substantially different from those described above but which, due to the degeneracy of the genetic code, still encode at least one Anti-CD22 antibody as described herein and/or as known in the art. Of course, the genetic code is well known in the art. Thus, it would be routine for one skilled in the art to generate such degenerate nucleic acid variants that code for specific Anti-CD22 antibodies of the present invention. See, e.g., Ausubel, et al., supra, and such nucleic acid variants are included in the present invention. Non-limiting examples of isolated nucleic acid molecules of the present invention include SEQ ID NOS: 1-16 and 33-48; corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an Anti-CD22 antibody can include, but are not limited to, those encoding the amino acid sequence of an antibody fragment, by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; or Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells

The present invention also relates to vectors that include isolated nucleic acid molecules of the present invention, host cells that are genetically engineered with the recombinant vectors, and the production of at least one anti-CD22 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Production of an Antibody

At least one Anti-CD22 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989). Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one anti-CD22 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Antibodies of the present invention can additionally be prepared using at least one Anti-CD22 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

Purification of an Antibody

An Anti-CD22 antibody can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT®, flow cytometry, immunocytology, Biacore® analysis, Sapidyne KinExA™ kinetic exclusion assay, SDS-PAGE and Western blot, or by HPLC analysis as well as by a number of other functional assays disclosed herein.

Cloning and Expression of CD22 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

Cloning and Expression in CHO Cells

The isolated variable and constant region encoding DNA and the dephosphorylated vector are ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot, ELISA, or by reverse phase HPLC analysis.

Anti-CD22 Antibody Compositions

The present invention also provides at least one Anti-CD22 antibody composition comprising at least one, at least two, at least three, at least four, at least five, at least six or more Anti-CD22 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-CD22 antibody amino acid sequence selected from the group consisting of 70-100% of the contiguous amino acids of the CDR regions of the antibodies described herein, or specified fragments, domains or variants thereof. Preferred Anti-CD22 antibody compositions include at least one or two full length, fragments, domains or variants as at least one CDR or LBR containing portions of the anti-CD22 antibody sequences described herein. Further preferred compositions comprise 40-99% of at least one of 70-100% of a CDR region of an Anti-CD22 Ab described herein. Such composition percentages are by weight, volume, concentration, molarity, or molality as liquid or dry solutions, mixtures, suspension, emulsions or colloids, as known in the art or as described herein.

Anti-CD22 antibody compositions of the present invention can further comprise at least one of any suitable and effective amount of a composition or pharmaceutical composition comprising at least one Anti-CD22 antibody to a cell, tissue, organ, animal or patient in need of such modulation, treatment or therapy, optionally further comprising at least one selected from at least one TNF antagonist (e.g., but not limited to a TNF antibody or fragment a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteroid, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen®), a sargramostim (GM-CSF, Leukine®), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme®), a cytokine or a cytokine antagonist. Non-limiting examples of such cytokines include, but are not limited to, any of IL-1 to IL-34. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-CD22 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the anti-CD22 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-CD22 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, Anti-CD22 antibody compositions of the invention can include polymeric excipients/additives such as polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN® 20" and "TWEEN® 80"), lipids (e.g., phospholipids, fatty acids), steroids (e.g., cholesterol), and chelating agents (e.g., EDTA).

These and additional known pharmaceutical excipients and/or additives suitable for use in the Anti-CD22 antibody, portion or variant compositions according to the invention are known in the art, e.g., as listed in "Remington: The Science & Practice of Pharmacy", 19.sup.th ed., Williams & Williams, (1995), and in the "Physician's Desk Reference", 52 ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one Anti-CD22 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one Anti-CD22 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one Anti-CD22 antibody, and a second vial comprising an aqueous diluent of prescribed buffer or preservative, wherein said packaging material comprises a label that instructs a patient to reconstitute the at least one Anti-CD22 antibody in the aqueous diluent to form a solution that can be held over a period of twenty-four hours or greater.

The at least one Anti-CD22 antibody used in accordance with the present invention can be produced by recombinant means, including from mammalian cell or transgenic preparations, or can be purified from other biological sources, as described herein or as known in the art.

The range of at least one Anti-CD22 antibody in the product of the present invention includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween® 20 (polyoxyethylene (20) sorbitan monolaurate), Tween® 40 (polyoxyethylene (20) sorbitan monopalmitate), Tween® 80 (polyoxyethylene (20) sorbitan monooleate), Pluronic® F68 (polyoxyethylene polyoxypropylene block copolymers), and PEG (polyethylene glycol) or non-ionic surfactants such as polysorbate 20 or 80 or poloxamer 184 or 188, Pluronic® polyols, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-CD22 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-CD22 antibody and preservative in an aqueous diluent is carried out using conventional dissolution and mixing procedures. To prepare a suitable formulation, for example, a measured amount of at least one anti-CD22 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one Anti-CD22 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one Anti-CD22 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one Anti-CD22 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one Anti-CD22 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those peninjector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system including those pen-injector systems for reconstituting a lyophilized drug in a cartridge for delivery of the reconstituted solution such as the Humatro-Pen®.

The products presently claimed include packaging material. The packaging material provides, in addition to the information required by the regulatory agencies, the conditions under which the product can be used. The packaging material of the present invention provides instructions to the patient to reconstitute the at least one Anti-CD22 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one Anti-CD22 antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one Anti-CD22 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one Anti-CD22 antibody in either the stable or presented formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

CD22 is a member of the Siglec sialic acid binding protein receptor superfamily that expressed is a highly specific manner on developing B-cells and on a variety of B-cell cancers including lymphomas and acute and chronic lymphocytic leukemias (Crocker et al, Nature Reviews Immunology 7, 255-266, 2007). Anti-CD22 antibodies have been found to negatively regulate growth of CD22 expressing B-cells and are implicated in the treatment of a variety of diseases. CD22 antibodies have been tested in clinical trials in patients with B-cell dependent autoimmune diseases and in patients with CD22-expressing hematologic cancers. Certain antibodies have been shown to induce tyrosine phosphorylation of CD22, a process that stimulates negative growth signals that block cell replication. In addition, CD22 antibodies have been shown to be internalized within the intracellular secretion pathway and lysosomes. Therefore, a high affinity human antibody to CD22 that has potent negative growth regulation properties that is rapidly internalized would be desirable to be used in CD22 related diseases such as hematologic cancers, SLE, rheumatoid arthritis, multiple sclerosis as well as other B-cell dependent autoimmune diseases. Anti-CD22 Abs or any derivatives of these mAbs including chimeric or humanized, or fragments can be used treatment of non-Hodgkin's lymphoma, other lymphomas and lymphoproliferative disorders, acute and chronic lymphocytic leukemias and other diseases in which CD22 has been implicated. These antibodies can be used either as a single agent or in combination with other therapeutic agents. They can also be used in combination with other tumor-immunomodulating agents such as IL-2, IL-12 and/or IFNalpha. Additionally, the Anti-CD22 antibodies can be used in combination with other monoclonal antibodies such as anti-TNF-$\alpha$, IL-12/IL-23, IL-2, GpIIb/IIIa receptor, CD52, CD20, RSV proteins, HER2/neu receptor, and the like; as well as with commercially approved antibodies including Rituxan®, Herceptin®, Mylotarg®, Campath®, Zevalin®, Bexxar®, Erbitux®, Avastin®, and Vectibix®.

These antibodies can be used either as a single agent or in combination with other therapeutic agents. They can also be used in combination with other tumor-immunomodulating agents such as IL-2, IL-12, GM-CSF and/or IFNalpha. Additionally, the Anti-CD22 antibodies can be used in combination with other monoclonal antibodies such as anti-TNF-$\alpha$, IL-12/IL-23, IL-2, GpIIb/IIIa receptor, CD52, CD20, RSV proteins, HER2/neu receptor, and the like; as well as with commercially approved antibodies including Rituxan®, Herceptin®, Mylotarg®, Campath®, Bexxar®, Erbitux®, Avastin® and Vectibix®.

Thus, the present invention also provides a method for modulating or treating at least one CD22 related disease, in a cell, tissue, organ, animal, or patient, as known in the art or as described herein, using at least one anti-CD22 antibody of the present invention.

CD22 is known to be expressed at high levels on B-cell cancers and dysplasias and may regulate autocrine or a paracrine mechanism involving induction of apoptosis of the malignant cells. B-cell cancers expressing CD22 at high levels include, but is not limited to, diffuse large B-cell lymphomas (DLBC), follicular lymphomas, Acute and chronic B-cell lymphocytic leukemias (ALL/CLL), mucosal associated lymphoid tract lymphomas (MALT), Mantle cell lymphoma, Burkitt lymphoma and other lymphoplasmocytic proliferactions (WHO classification of tumours, 2001). Anti-CD22 antibodies could therefore be used to treat these diseases alone or in combination with other chemotherapeutic and B-cell targeted biotherapeutics. In addition, other B-cell dependent autoimmune disease in which B-cell producted autoantibody formation is implicated is disease, such as systemic lupus erythematosus (SLE), Rheumatoid arthritis (RA), multiple sclerosis (MS), could be treated with anti-CD22 antibodies.

The ability, of antibodies directed to CD22 to modulate tumor cell survival and disease progression was confirmed by the inhibitory effects of an anti-CD22 mAb on tumor growth both in vitro and in vivo. It was reported that binding of certain anti CD22 antibodies to CD22 expressing lymphoma cells can inhibit growth in vitro (Stein et al Epitope specificity of the anti-B-cell lymphoma monoclonal antibody, LL2. Cancer Immunol. Immunother., 37:293, 1993). The murine anti-CD22 MAb (originally designated EPB-2 and now called LL2) can be humanized and used for imaging and treatment of NHL or chronic lymphatic leukemia. Immunohistological studies revealed that LL2 is reactive with virtually all cases of NHL, including diffuse and nodular, poorly differentiated lymphocytic lymphomas, and histiocytic large cell lymphomas. LL2 has a highly restricted specificity, being reactive with only the B-cell population of the germinal center of normal lymph nodes and the white pulp of the spleen, but not with megakaryocytes, myeloid, or erythroid cells in the bone marrow. Moreover, LL2 is not reactive with any peripheral blood cells, including the blood's normal B cells, or with any other normal tissue. LL2 also has other unique features related to its target antigen, differentiating it from other anti-B-cell lymphoma antibodies. In vitro studies have demonstrated clearly that LL2 is internalized after binding to its CD22 target antigen on the surface of Raji lymphoma cell lines, and that the antigen is reexpressed rapidly on the cell surface. A humanized for of murine monoclonal antibody, known as Epratuzumab, has immunomodulatory and growth modulatory effects on human lymphoma cell lines (Carnahan et al., Molecular Immunology 44: 1331, 2007) al. 2001). Anti-CD22 monoclonal antibody CD22 can also be a prognostic factor and a marker for malignancies. CD22 is expressed at high levels in virtually all lymphomas, and on most ALL and CLL B-cell leukemias. CD22 expression in increased in patient tumors following treatment of the CD20 target therapeutic antibody Rituxan® suggesting CD22 target antibodies could be used to treat Rituxan® resistant and relapsed patients (Micallef et al., Blood 118:4053, 2011).

CD22 is hypothesized to be a causative factor in cancer-related morbidity such as asthenia/cachexia and bone resorption. Tumor-induced cachexia (Cahlin et al. 2000) and bone resorption (subsequent hypercalcemia) (Sandhu et al. 1999) were found to be diminished in CD22 knockout mice. Cancer-associated depression and cerebral edema secondary to brain tumors have also been associated with high levels of CD22 (Musselman et al. 2001). Anti-CD22 antibodies of the invention also can inhibit human melanoma and human prostate carcinoma induced cachexia in nude mice.

The present invention includes a method for modulating or treating at least one malignant disease in a cell, tissue, organ, animal or patient, including, but not limited to, at least one of: non-Hodgkin's lymphoma, Burkit lymphoma, leukemia, acute leukemia, acute lymphoblastic leukemia (ALL), B-cell, chronic lymphocytic leukemia (CLL), and hairy cell leukemia. Such a method can optionally be used in combination with, by administering before, concurrently or after administration of such CD22 antibody, radiation therapy, an anti-angiogenic agent, a chemotherapeutic agent, a farnesyl transferase inhibitor or the like.

The present invention also provides a method for modulating or treating at least one CD22 mediated immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, asteoarthritis, inflammatory bowel disease, ulverative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, hone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Therapeutic Treatments

Any method of the present invention can comprise a method for treating a CD22 mediated disorder, comprising administering an effective amount of a composition or pharmaceutical composition comprising at least one Anti-CD22 antibody to a cell, tissue, organ, animal or patient in need of such modulation, treatment or therapy. Such a method can optionally further comprise co-administration or combination therapy for treating such immune diseases, wherein the administering of said at least one Anti-CD22 antibody, specified portion or variant thereof, further comprises administering, before concurrently, and/or after, at least one agent as described above.

Typically, treatment of pathologic conditions is effected by administering an effective amount or dosage of at least one Anti-CD22 antibody composition that total, on average, a range from at least about 0.01 to 500 milligrams of at least one Anti-CD22 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 .mu.g/ml serum concentration per single or multiple administration. Suitable dosages are known to medical practitioners and will, of course, depend upon the particular disease state, specific activity of the composition being administered, and the particular patient undergoing treatment in some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 1.6, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

Parenteral Formulations and Administration

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable Pharmaceutical Carriers are Described in the Most Recent Edition of Remington's Pharmaceutical Sciences, A. Osol, a Standard Reference Text in this Field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of at least one Anti-CD22 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one Anti-CD22 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90, Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one Anti-CD22 antibody composition is delivered in a particle size effective for reaching the lower airways of the lung or sinuses. According to the invention, at least one Anti-CD22 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin®, metered dose inhaler, typically use a propellant gas and require actuation during inspiration (See, e.g., WO 94/16970, WO 98/35888). Dry powder inhalers like Turbuhaler® (Astra), Rotahaler® (Glaxo), Diskus® (Glaxo), Spiro® inhaler (Dura), devices marketed by Inhale Therapeutics, and the Spinhaler®, powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx®, Aradigm, the Ultravent®, nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one Anti-CD22 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1-5 µm, for good respirability.

Administration of CD22 Antibody Compositions as a Spray

A spray including CD22 antibody composition protein can be produced by forcing a suspension or solution of at least one Anti-CD22 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one Anti-CD22 antibody composition protein delivered by a sprayer have a particle size less than about 10 μm, preferably in the range of about 1 μm to about 5 μm, and most preferably about 2 μm to about 3 μm.

Formulations of at least one Anti-CD22 antibody composition protein suitable for use with a sprayer typically include antibody composition protein in an aqueous solution at a concentration of about 0.1 mg to about 100 mg of at least one Anti-CD22 antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as CD22 antibodies, or specified portions, or variants, can also be included in the formulation.

Administration of CD22 Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 μm, preferably in the range of about 1 μm to about 5 μm, and most preferably about 2 μm to about 3 μm.

Formulations of at least one Anti-CD22 antibody suitable for use with a nebulizer, either jet or ultrasonic, typically include a concentration of about 0.1 mg to about 100 mg of at least one Anti-CD22 antibody protein per ml of solution. The formulation can include agents such as an excipient, a buffer, an isotonicity agent, a preservative, a surfactant, and, preferably, zinc. The formulation can also include an excipient or agent for stabilization of the at least one Anti-CD22 antibody composition protein, such as a buffer, a reducing agent, a bulk protein, or a carbohydrate. Bulk proteins useful in formulating at least one Anti-CD22 antibody composition proteins include albumin, protamine, or the like. Typical carbohydrates useful in formulating at least one anti-CD22 antibody include sucrose, mannitol, lactose, trehalose, glucose, or the like. The at least one Anti-CD22 antibody formulation can also include a surfactant, which can reduce or prevent surface-induced aggregation of the at least one Anti-CD22 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of CD22 Antibody Compositions by a Metered Dose Inhaler

In a metered dose inhaler (MDI), a propellant, at least one Anti-CD22 antibody, and any excipients or other additives are contained in a canister as a mixture including a liquefied compressed gas. Actuation of the metering valve releases die mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one Anti-CD22 antibody for use with a metered-dose inhaler device will generally include a finely divided powder containing at least one Anti-CD22 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one anti-CD22 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one Anti-CD22 antibody compositions via devices not described herein.

Oral Formulations and Administration

Formulations for oral administration rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug deliver systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat.

No. 5,879,681 and U.S. Pat. No. 5,871,753 are used to deliver biologically active agents orally are known in the art.

Mucosal Formulations and Administration

For absorption through mucosal surfaces, compositions and methods of administering at least one Anti-CD22 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomach, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one Anti-CD22 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Abbreviations:
BSA—bovine serum albumin
EIA—enzyme immunoassay
FBS—fetal bovine serum
$H_2O_2$—hydrogen peroxide
HRP—horseradish peroxidase
Ig—immunoglobulin
CD22—ICD22
IP—intraperitoneal
IV—intravenous
Mab—monoclonal antibody
OD—optical density
OPD—o-Phenylenediamine dihydrochloride
PEG—polyethylene glycol
PSA—penicillin, streptomycin, amphotericin
RT—room temperature
SQ—subcutaneous
v/v—volume per volume
w/v—weight per volume Example 1. Affinity and Quantitation ELISAs Nunc-Immuno® MaxiSorp® 96 well plates were coated with 100 µl of 2 µg/ml, 0.2 µg/ml, 0.02 µg/ml or 0.002 µg/ml recombinant CD22 extracellular domain (PeproTech, Inc. catalog number 100-01 in coating solution (sodium bicarbonate in PBS). The plates were covered with plate sealer and incubated at 4° C. overnight. Plates were emptied and the residual liquid tapped out on paper towels. 200 µl washing solution (0.05% Tween®-20 in PBS) was added and shaken at 200 RPM for 5 min at room temperature. The plates were emptied and residual liquid tapped out on paper towels. 200 µl blocking solution (2% Carnation milk in PBS) was added and shaken at 200 RPM for one hour at room temperature. Plates were emptied and residual liquid tapped out on paper towels. 100 µl of diluted samples containing VM1000, VM1001, VM1002, VM1003, VM1004, VM1005, VM1006, VM1007, VM1008, VM1009, VM1010, VM1011, VM1012, VM1013, VM1014, and VM1015 antibodies for ELISA were used. The samples were shaken at 200 RPM for one hour at room temperature; plates emptied and residual liquid tapped out on paper towels. 200 µl washing solution (0.05% Tween®-20 in PBS) was added, shaken at 200 RPM for 5 min at room temperature; plates emptied and residual liquid tapped out on paper towels. This process was repeated three times. 100 µl of 1:2500 dilution of anti-human IgG conjugated with HRP diluted in block solution (2% Carnation milk in PBS) was added for all samples. 100 µl of 1:2500 dilution of anti-rabbit IgG conjugated with HRP diluted in block solution (2% Carnation milk in PBS) was added for control antibody. The contents were shaken at 200 RPM for one hour at room temperature, plates emptied and residue liquid tapped out on paper towels. 200 µl washing solution (0.05% Tween®-20 in PBS) was added, shaken at 200 RPM for 5 min at room temperature; plates emptied and residual liquid tapped out on paper towels. This process was repeated three times. 100 µl TMB substrate solution was added, and incubated at room temperature. The reaction was stopped with 1 N HCl, and the plate read at 450 nm to determine relative binding affinity (FIG. 17).

Quantitation ELISA

Example 2. CHO—S Cells Transfection

One week before transfection, CHO—S cells (Invitrogen) were transferred to monolayer culture in serum supplemented Dulbecco's Modified Eagle Medium (D-MEM) (Invitrogen). One day before transfection, cells are plated $0.4 \times 10^5$ cells in 100 uL of serum supplemented D-MEM per transfection sample in 96 well formats. Prepared DNA-Lipofectamine complexes for each transfection sample. Diluted 0.25 ug of DNA in 25 uL Opti-MEM Reduced Serum Medium and mixed gently, and incubated at room temperature for 5 min. Diluted 0.5 uL Lipofectamine 2000 (Invitrogen) in 25 uL Opti-MEM Reduced Serum Medium. Mixed gently and incubated at room temperature for 5 min. Combined the diluted DNA with the diluted Lipofectamine. Mixed gently and incubated for 20 min at room temperature. Added the 50 uL DNA-Lipofectamine complexes to each well containing cells and medium. Mixed gently by rocking the plate. Incubated the cells at 37 C in a 5% $CO_2$ incubator overnight. Aspirated medium in each well. Added 100 uL of serum supplemented D-MEM to each well. Collected supernatant for ELISA assay and cell lysate for beta-galactosidase assay.

Example 3. Antibody Purification from Cell Culture Supernatant

The following buffers were prepared in a standard fashion. Binding buffer 10 mM $Na_2HPO_4/NaH_2PO_4$, pH 7.0. Elution Buffer: 12.5 mM Citric Acid, pH 2.7 (use $Na_3$-citrate). Neutralization Buffer: 0.5 M $Na_2HPO_4/NaH_2PO_4$, pH 8.0. 20% Ethanol and water. All buffers were filtered before use (0.45 µm). Supernatants were purified using an ÄKTA™ FPLC™ system fitted with a HiTrap™ Protein G Sepharose HP (1 mL volume) column. For Sample loading, loading tubes are rinsed with ethanol (20 mL, 5 mL/min), then binding buffer (20 mL, 5 mL/min). Protein G column is attached to system and rinsed with binding buffer (10 mL, 1 mL/mn). The sample is loaded at 1 mL/min or slower (for overnight loading). After loading, the column is detached and loading tubes are rinsed with water (20 mL, 5 mL/mn) and then 20% ethanol (20 mL, 5 mL/min). For antibody purification, the AKTA™ system was washed (pump A and all tubing) with binding buffer. Collection tubes were prepared for fraction collection by adding 50 µl Neutralization buffer to each tube. The protein G column was attached to the system. The flow was set to 1 mL/min, and run until baseline was stable. The column valve was switched to position 3. The column was washed with binding buffer (10 mL minimum) until baseline was reached. The pump was stopped and washed with water, then with Elution buffer. The flow was set to 1 ml/min, and run until baseline was stable. The column valve was switched to position 3 and the fraction collector was started (0.5 mL fractions). Fractions were collected until base line was reached at which point the system was stopped. The elution profile was copied to the clipboard and into WORD document. The pump was washed with water; then with binding buffer. The protein G column was washed with binding buffer (10 mL). The pump was washed with 20% Ethanol. The column was washed with 20% Ethanol (20 mL) stored in the coldroom.

The antibodies were reconstituted in sterile 1×PBS, pH 7.4, 0.02% sodium azide, 10 mg/mL BSA. The antigen was CD22 (21,000 kDa) in four separate vials at 0.5 mg, 1 mg, 0.5 mg and 0.5 mg, was diluted with sterile 1×PBS, pH 7.4, 0.02% sodium azide to 375 ug/mL, 1 mg/mL, 500 ug/mL and 500 ug/mL. The label, Cy5-conjugated AffiniPure goat anti-human IgG (H+L), Cy5, 1.5 µg/mL, was purchased from Jackson ImmunoResearch (West Grove, Pa.). The label was reconstituted in sterile 1×PBS, pH 7.4, 0.02% sodium azide, and diluted to 0.500 mg/mL. The Running Buffer was 1×PBS, pH 7.4, 0.02% sodium azide. The Sample Buffer was 1×PBS, pH 7.4, 0.02% sodium azide, 1 mg/mL Bovine Serum Albumin (BSA). The PMMA beads (Part#440197/Lot3257) were provided by Sapidyne Instruments, Inc. (Boise, Id.) and coated with capture reagent in the following fashion. Beads were aliquoted dry into 200 mg portions and rocked in 1 mL coating solution (30 ug/mL BAP001 in running buffer) for 2 hours. Beads were then rocked 1 hour in blocking solution (10 mg/mL BSA in running buffer) and stored at 4° C.

For Equilibrium Analysis, PMMA beads coated with CD22 were used to capture a portion of the free receptor from equilibrated sample of receptor (anti-CD22 antibody) and ligand (antigen; CD22). For each data point a fresh column of ligand-coated beads was introduced into the flow cell. The equilibrated sample was rapidly drawn past the column to minimize the contact time with the immobilized ligand. This ensured the contact time with the immobilized ligand does not disrupt the sample equilibrium. The immobilized ligand thus acted as a probe to capture free receptor in solution. Captured antibodies were detected with fluorescently labeled anti-human secondary antibody. Unbound reagents were washed away, leaving a signal that is proportional to free receptor in the equilibrated sample. The fluorescence was converted to voltage that is directly proportional to the amount of free receptor (antibody) in the equilibrated sample. Experiments were run at both high and low concentrations of receptor, then utilized together in an n-curve analysis for optimal results. For the Direct Method of Kinetic Analysis, the same immobilized ligand (CD22 coated PMMA) was used as the capture reagent for kinetic experiments as for equilibrium experiments. The amount of free receptor (antibody) in the sample was measured pre-equilibrium, yielding data points that monitor the decrease in free receptor (antibody) over time as the sample moves toward equilibrium. FIG. 33 shows a table with data from Sapidyne analysis of the top 10 hits for anti-IL6 antibodies BAP001-clone 1 to BAP001-clone 10 compared to BA003 (CNTO136).

Example 4. Surface Plasmon Resonance Determination of Affinity Constants to Recombinant CD22 Extracellular Domain of the Anti-CD22 Antibodies of the Invention BIAcore® 3000, GE Healthcare was used to determine binding curves and kinetic parameters. An anti-human Fc (1.8 mg/ml) was diluted to a concentration of 50 ug/ml in NaOAc buffer (10 mM, pH 4.8) and coupled to the carboxymethylated dextran matrix of a CM-5® sensor chip using the manufacturer's amine-coupling chemistry as described in the BIAcore® systems manual. Using the surface preparation wizard aiming for 10000RU, the carboxyl groups on the sensor surfaces were first activated with NHS/EDC followed by the addition of the anti-human Fc. The remaining activated groups were blocked by the injection of 1M ethanolamine. Each of the flow cells was coupled individually. Employing these conditions, the four flow cell surfaces containing 7554-9571 RU of anti-human Fc were prepared. In preliminary experiments, it was determine that three injections (15 µl at 30 µl/min) 100 mM $H_3PO_4$/0.05%

CHAPS would efficiently remove the bound immunoglobulin and preserve the binding capacity of the immobilized anti-human Fc.

Experiments were performed on the BIAcore 3000 at 25° C. and a flow rate of 30 ul/min. The antibody candidate was dissolved in HBS (10 mM HEPES with 0.15M NaCl, 3.4 mM EDTA, and 0.05% surfactant P20 at pH 7.4) at 5 ug/ml. The analyte, CD22, was dissolved in HBS at 0.25, 0.125, 0.062, 0.031 and 0.015 ug/ml. 3*30 ul of 5 ug/ml of antibody BA001 was flowed over its respective flow cell followed by injections of 240 ul of each CD22 concentration at 30 ul/min (association phase) and an uninterrupted 1200 seconds of buffer flow (dissociation phase). The surface of the chip was regenerated by three sequential injections of 15 ul each with 100 m M $H_3PO_4$/0.05% CHAPS. The injections of HBS serve as a reference (blank sensogram) for the subtraction of bulk refractive indices for analysis. Using the 1:1 model in BIAevaluation 4.1, both a local fit and global fit was done for both dissociation (kd, [s−1] and association (ka, [$M^{-1}s^{-1}$]) and the dissociation constant (KD, [M]) calculated (kd/ka).

Analysis was done using BIAeveluation version 3.0. Kinetic constants were derived from sensogram data by fitting the experimental curves to the rate equations derived from models of the interaction mechanisms. A global analysis using a 1:1 binding model with local RUmax fit, the ka, kd, and KD were determined.

The following equations were utilized:

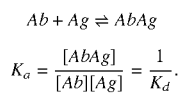

$$Ab + Ag \rightleftharpoons AbAg$$
$$K_a = \frac{[AbAg]}{[Ab][Ag]} = \frac{1}{K_d}.$$

Biacore data for humanized anti-CD22 monoclonal antibodies before affinity maturation is set forth in FIG. 18 (BA006G). After BA600G affinity maturation and subsequent humanization selected clones were tested by Biacore analysis as shown in FIG. 18.

Example 5. Anti-CD22 Selected Anti-CD22 Antibodies Bind to Cell Surface CD22 Expressed in Lymphoma Cell Lines and Induce Internalization The CD22 protein has been shown to be expressed in developing B cells and in most human non-Hodgkin's lymphoma cell lines, including Daudi, RAMOS and RAJI B cell lines (Knowles D. M., Chadburn A., Inghirami G. Immunophenotypic markers useful in the diagnosis and classification of hematopoietic neoplasms Knowles D. M. eds. Neoplastic Hematopathology, 73-95, Williams & Wilkins Baltimore 1992). Binding of anti-CD22 antibodies to B cell lines, or primary B cells from healthy individuals and patients with non-Hodgkin's lymphoma (NHL), results in rapid internalization of the CD22/antibody complex. Internalization appears to be faster at early time points in cell lines than in primary B cells and NHL patient-derived B cells, but the maximum internalization reached is comparable for all B cell populations after several hours of treatment and appears to reach saturation at higher antibody concentrations.

Anti-CD22 monoclonal antibodies selected herein, clones VM1000, VM1001, VM1002, VM1003, VM1004, VM1005, VM1006, VM1007, VM1008, VM1009, VM1010, VM1011, VM1012, VM1013, VM1014, and VM1015 of the invention, were tested for their ability to bind cell surface expressed CD22 in Daudi, RAMOS and RAJI B lymphoma cell lines as determined by fluorescent activated cell sorting analysis. Cell cultures were maintained in exponential growth in RPMI 1640 media containing fetal bovine serum prior to analysis. Anti-CD22 expression levels were determined by 10% ELISA and FACS analysis using commercially available anti-CD22 antibodies conjugated to phycoerythrin (PE) (Becton Dickenson, catalog number 340708). For baseline surface expression, 1×10e6 Daudi cells (for example) were incubated with PBS containing 2% FBS and 12 μg/μl anti-CD22-PE conjugate for 45 min on ice, then washed with ice-cold PBS-FBS solution. Cells were then analyzed by FACS using standard procedures to quantitate surface binding in the target cell population.

In parallel, Daudi cells, 1×10e6 were treated with similar concentrations of the selected anti-CD22 Mab clones VM1000, VM1001, VM1002, VM1003, VM1004, VM1005, VM1006, VM1007, VM1008, VM1009, VM1010, VM1011, VM1012, VM1013, VM1014, and VM1015 of the invention. in PBS-FBS solution for 20 hours at 37 C to allow for binding and internalization. After this period, the cells were washed, and then exposed to 12 μg/ml anti-CD22-PE conjugate in PBS-FBS solution on ice. Under these conditions, residual surface CD22 would be detected and quantitated using FACS analysis as described above. Shown in FIG. 19A is a typical result for an anti-CD22 antibody of the invention. After exposure for 20 hours there is a decrease in surface CD22 expressions as measured as a shift in the fluorescent population to the left indicating lower levels of detection. The decrease in the relative amounts of CD22 surface express can be expressed as a ration of the two populations.

Shown in FIG. 19B are the results of evaluation of a panel of anti-CD22 antibodies for their ability to internalize CD22 receptor upon exposure for 20 hours at 37 C and determined by the percentage shift in anti-CD22-PE conjugate binding after prior exposure. A spectrum of changes in CD22 expression is detected as visualized by the shift in the CD22 positive population to the left. Quantitation of the extent of internalization is shown if FIG. 20. Individual anti-CD22 clones selected anti-CD22 Mab clones VM1000, VM1001, VM1002, VM1003, VM1004, VM1005, VM1006, VM1007, VM1008, VM1009, VM1010, VM1011, VM1012, VM1013, VM1014, and VM1015 of the invention were analysed as described above and the relative extent of CD22 internalization was expressed as a percent shift in the population over baseline following antibody exposure.

Example 6. Measurement of Rapid Internalization of Anti-CD22 Antibodies of the Invention by Quantitative Confocal Immunofluorescent Microscopy in Lymphoma Cell Lines Daudi cells were maintained under conditions of exponential growth in RPMI 1640 media containing 10% FBA at 37 C, and then harvested for analysis. Selected antiCD22 selected anti-CD22 Mab clones VM1000, VM1001, VM1002, VM1003, VM1004, VM1005, VM1006, VM1007, VM1008, VM1009, VM1010, VM1011, VM1012, VM1013, VM1014, and VM1015 of the invention were directly conjugated to FITC using the Zenon labeling complex (Molecular Probes) using the manufacturer's recommended procedures. Approximately 1×10e7 Daudi cells were resuspended in PBS containing 5 μg/ml labeled anti-CD22 antibody and incubated for 45 minutes on ice. Cells then washed twice in PBS-FBS solution at 0 C. Cells were then incubated in RPMI 1640 media containing 10% FBS for varying periods at 37 C, harvested and washed in PBS at 0 C. The cells were then briefly fixed in 4% paraformaldehyde solution for 5 min at room temperature, then washed in PBS containing 0.05% Triton® X-100. Cell pellets were collected by centrifugation and resuspended in a minimal volume of FBS neat, and then applied to glass microscope slides. Prior to analysis, slides were treated with mounting fluid containing the nuclear stain DAPI, then coverslips were applied.

Confocal images were recorded using an ACAS Ultima confocal microscope (Meridian Instruments, Inc., Okemos, Mich.) and represent 1-μm sections through the center of a focal plane using a 100× oil immersion objective.

The Anti-CD22 monoclonal antibodies selected clones VM1000, VM1001, VM1002, VM1003, VM1004, VM1005, VM1006, VM1007, VM1008, VM1009, VM1010, VM1011, VM1012, VM1013, VM1014, and VM1015 of the invention were analysed for their ability to be rapidly internalized into the intracellular compartment as judged by immunofluorescent signal on the cell surface versus the intracellular endocytotic compartment. The antibodies of the invention were compared to BA006H, and humanized version of the murine monoclonal antibody LL2. In this example, FIG. 21A, the anti-CD22 antibodies of the invention bind to CD22 protein expressed on the surface of Daudi cells by approximately 20-fold compared to BA006H as judged by relative mean fluorescence (RMF), and are virtually completely internalized within the cell with 90 minutes, localizing predominantly to within the perinuclear golgi apparatus and associated lysosomes. Shown in FIG. 21B is a chart of the RMF surface binding values obtained in this manner for individual anti-CD22 antibodies of the invention.

Example 7

Figure 22A:
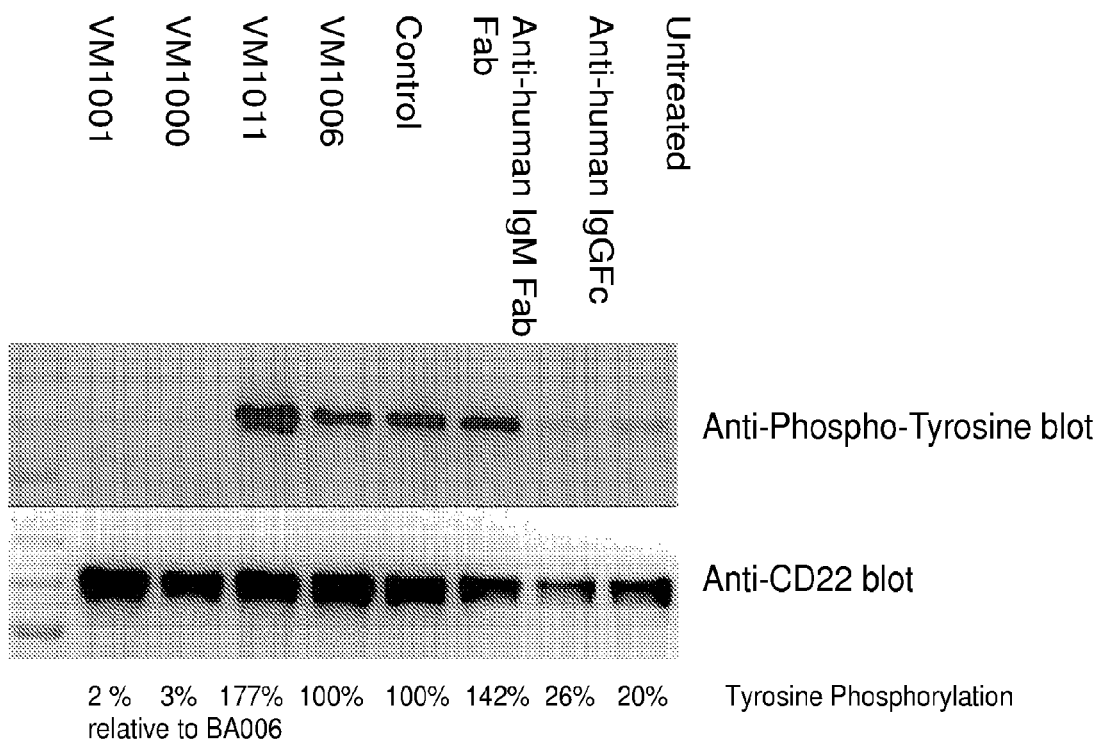
FIGS. 22A and 22B show induction of CD22 tyrosine phosphorylation of CD22 present on the surface of the human lymphoma cell line Daudi upon exposure to selected antibodies from VM1000, VM1001, VM1002, VM1003, VM1004, VM1005, VM1006, VM1007, VM1008, VM1009, VM1010, VM1011, VM1012, VM1013, VM1014, and VM1015 of the invention.
Figure 22B:
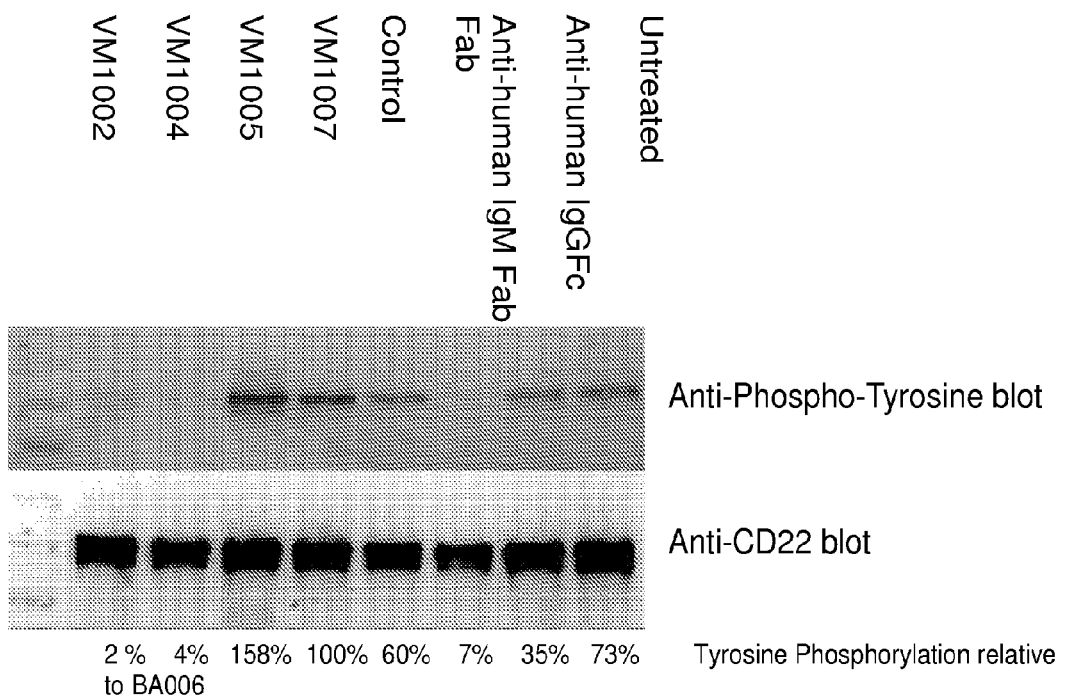

Stimulation of CD22 tyrosine phosphorylation following treatment of CD22 positive lymphoma cell lines Anti-CD22 monoclonal antibodies selected clones VM1000, VM1001, VM1002, VM1003, VM1004, VM1005, VM1006, VM1007, VM1008, VM1009, VM1010, VM1011, VM1012, VM1013, VM1014, and VM1015 of the invention. Anti-CD22 antibodies have previously been shown to bind to cells expressing CD22 and stimulate the tyrosine phosphorylation of they cytoplasmic region of the receptor (Carnahan et al, Clin Cancer Res Sep. 1, 2003 9; 3982s). This bioactivity of anti-CD22 antibodies has been associated with negative regulation of the BCR signaling complex resulting in decreased lymphoma cell growth and induction of cell death. The anti-CD22 antibodies selected were therefore analyzed for their ability to stimulate CD22 tyrosine phosphorylation upon exposure to receptor expressing cell lines. Daudi cells were maintained in exponential growth by culturing in RPMI 1640 containing 10% FBS before harvesting and treatment with anti-CD22 antibodies. The treated cells were then lysed with detergent buffer and CD22 was immunoprecipitated using anti-CD22 BA006H then subjected to SDS-PAGE and Western blot analysis. The resulting blots were then probed with anti-phosphotyrosine antibodies (4G10) or with rabbit polyclonal anti-CD22 (Santa Cruz, Catalog number SC-7932. FIGS. 22 A and B show the result of these analyses. The ratio of tyrosine phosphorylated CD22 protein to total CD22 are indicated below each antibody treatment. As a control, Daudi cells were treated with an anti-IgM antibody to engage and stimulate the B-cell receptor complex as a means to saturate the potential to trans-phosphorylate the CD22 cytoplasmic domain.

Figure 23:
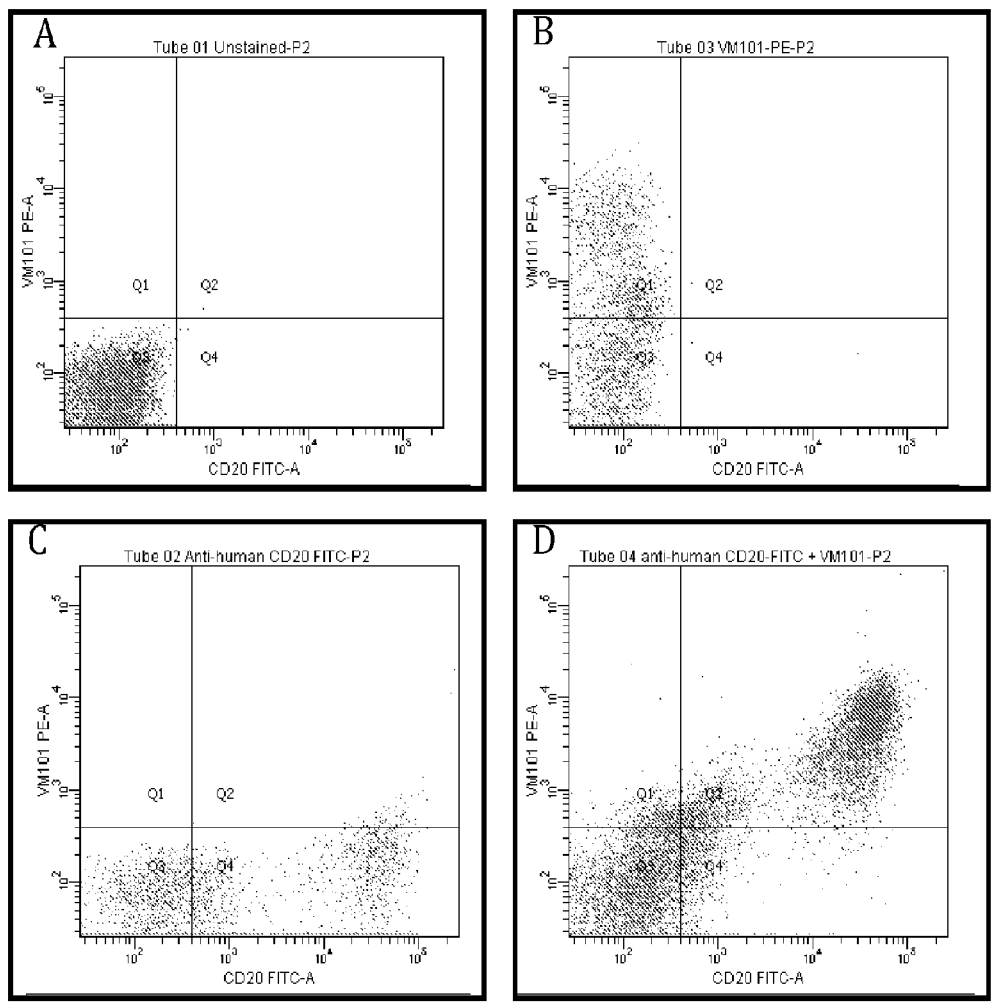
FIG. 23 shows data demonstrating cross reactivity of anti-CD22 antibodies to CD22 expressed on cells of the primate species, cynomologus macaques (*Macaca fascicularis*). The cells for each test condition were washed in PBS, and then fixed with 4% formaldehyde in PBS for 10 min at room temperature. The cells were then resuspended in 0.5 ml of PBS containing 2% FBS then analyzed for CD22 and CD20 surface staining by fluorescent activated cell sorting (FACS) analysis (1). Cells treated with no antibody did not have an appreciable shift in fluorescent intensity in either the FITC or PE channels (1A), whereas cell stained with VM101-PE contained a CD22 positive population (1B). Similarly, cells stained with anti-CD20-FIT contained a CD20 positive population (1C). Cells stained with both VM101-PE and CD20-FITC antibodies have a double labeled population as one would expect based on the expression patterns of both antigen in PBMC's (1D). VM101 specifically recognizes the cynomologus CD22 protein.

Cross-reactivity. The surface protein CD22 is known to be expressed on the surface of developing B-cells and on lymphoma and leukemia cells derived from the B-cell lineages. The anti-CD22 antibodies of the present invention were evaluated for ability to cross-react with CD22 expressed on murine and rodent B-cells. Results indicate that there is no appreciable binding to the rodent form of the protein. Anti-CD22 antibodies of the present invention were also evaluated for cross reactivity to primate species, cynomologus macaques (*Macaca fascicularis*). Peripheral blood lymphocytes (PBMC's) isolated from cynomologus macaques (source Primate Biologicals, Inc., Bethesda, Md.) (enriched for CD22 positive B-cells) were analyzed. Anti-CD22 antibodies of the present invention (the anti-CD22 antibody designated as "VM101" in the data herein) were directly labeled with the fluorescent molecule phycoerythrin (PE). To test for positive staining, approximately 2.5×10e6 PBMC's for each test condition were washed in PBS then resuspended in PBS containing 10% fetal bovine serum (FBS). Cells were then exposed to either no antibody, anti-CD22 PE-labeled antibody (20 ug/ml), or anti-human CD20-FITC conjugated antibody which has been shown to cross-reacted with cynomologus CD20 (Miltenyl Biotech, catalog number 130-091-108 at 1:10 dilution of stock reagent), then incubated at 0 C for 60 min. The cells for each test condition were washed in PBS, and then fixed with 4% formaldehyde in PBS for 10 min at room temperature. The cells were then resuspended in 0.5 ml of PBS containing 2% FBS then analyzed for CD22 and CD20 surface staining by fluorescent activated cell sorting (FACS) analysis (FIGS. 23A-23C). Cells treated with no antibody did not have an appreciable shift in fluorescent intensity in either the FITC or PE channels (FIG. 23A), whereas cell stained with VM101-PE contained a CD22 positive population (FIG. 23B). Similarly, cells stained with anti-CD20-FIT contained a CD20 positive population (FIG. 23C). Cells stained with both VM101-PE and CD20-FITC antibodies have a double labeled population as one would expect based on the expression patterns of both antigen in PBMC's (FIG. 23D). VM101 specifically recognizes the cynomologus CD22 protein.

Example 9

Relative expression of Anti-CD22 antibodies. Anti-CD22 antibodies of the present invention were expressed in mammalian cells to determine if they have properties that are consistent with high level production in manufacturing processes to produce material for clinical studies. The expression of anti-CD22 antibodies of the present invention (Antibody 1, Antibody 2 and Antibody 3) were compared to a control antibody ("Control"), a humanized CD22 antibody. The resulting cells expressing each CD22 antibody were cultured for equivalent periods in mammalian cell culture conditions and the conditioned media was tested for the presence and yield of monoclonal antibody. The results were compared to a marketed antibody that is expressed at high level during these conditions (trastuzumab, also known as Herceptin®) and serves as a comparator. Table I shows the results of this test for expression and manufacturability under these conditions.

What is claimed is:

1. An isolated antibody or antibody fragment that binds to human CD22, comprising:
   (a) a heavy chain variable region comprising three heavy chain complementarity determining regions (CDR1, CDR2, CDR3), wherein the complementarity determining region 1 (CDR1) has the amino acid sequence of complementary determining region 1 of SEQ ID NO: 49, the complementarity determining region 2 (CDR2) has the amino acid sequence of complementary determining region 2 of SEQ ID NO: 49, and the complementarity determining region 3 (CDR3) has the amino acid sequence of complementary placement determining region 3 of SEQ ID NO: 49; and
   (b) a light chain variable region comprising three light chain complementarity determining regions (CDR4, CDR5, CDR6), wherein the complementarity determining region 4 (CDR4) has the amino acid sequence of complementary determining region 4 of SEQ ID NO: 17 or 32, the complementarity determining region 5 (CDR5) has the amino acid sequence of complementary determining region 5 of SEQ ID NO: 17, and the complementarity determining region 6 (CDR6) has the amino acid sequence of complementary determining region 6 of SEQ ID NO: 17;
   wherein the heavy chain variable region and the light chain variable region each have human framework regions surrounding the complementarity determining regions (CDR1, CDR2, CDR3, CDR4, CDR5, CDR6) of the heavy chain and light chain variable regions; and
   (c) a heavy chain constant region and a light chain constant region derived from one or more human antibodies and
   wherein the heavy chain constant region is associated with the heavy chain variable region and the light chain constant region is associated with the light chain variable region.

2. The antibody or antibody fragment according to claim 1, wherein said antibody or antibody fragment has a heavy chain variable region having the amino acid sequence of SEQ ID NOS: 49, 50, 51, 52, 53, 54, 55, 56, 57, 58, 59, 60, 61, 62, 63, or 64; a light chain variable region having the amino acid sequence of SEQ ID NOS: 17, 18, 19, 20, 21, 22, 23, 24, 25, 26, 27, 28, 29, 30, 31, or 32.

3. The antibody or fragment according to claim 1, wherein said antibody or fragment competitively inhibits in vivo binding of an anti CD22 murine antibody to human CD22.

4. The antibody or antibody fragment according to claim 1, wherein said antibody or antibody fragment binds human CD22 with an affinity ($K_d$) of at least $10^{-9}$ M.

5. The antibody or antibody fragment according to claim 1, wherein said antibody or antibody fragment substantially neutralizes at least one activity of said human CD22.

6. A composition, comprising said antibody or antibody fragment according to claim 1, and a carrier or diluent.

7. The antibody or antibody fragment of claim 1, wherein the complementary determining region 1 (CDR1) of the heavy chain variable region is at positions 26-35 of the amino acid sequence of SEQ ID NO: 49, the complementary determining region 2 (CDR2) of the heavy chain variable region is at positions 50-66 of the amino acid sequence of SEQ ID NO: 49, the complementary determining region 3 (CDR3) of the heavy chain variable region is at positions 99-105 of the amino acid sequence of SEQ ID NO: 49, the complementary determining region 4 (CDR4) of the light chain variable region is at positions 24-40 of the amino acid sequence of SEQ ID NO: 17 or 32, the complementary determining region 5 (CDR5) of the light chain variable region is at positions 56-62 of the amino acid sequence of SEQ ID NO: 17, and the complementary determining region 6 (CDR6) of the light chain variable region is at positions 95-102 of the amino acid sequence of SEQ ID NO: 17.

8. The antibody or antibody fragment according to claim 1, wherein said antibody or antibody fragment binds human CD22 with an affinity ($K_d$) of at least $10^{-11}$M.

9. The antibody or antibody fragment according to claim 1, wherein said antibody or antibody fragment binds human CD22 with an affinity ($K_d$) of at least $10^{-12}$ M.

10. A method for inhibiting binding or specific activity of CD22 in a cell, tissue, organ or animal having an immune condition, an immune disorder, an immune disease, or a cancerous disorder or cancerous condition, comprising:
contacting or administering an effective amount of at least one antibody or antibody fragment according to claim 1 with, or to, said cell, tissue, organ or animal.

11. The method according to claim 10, wherein said immune condition, immune disorder or immune disease is at least one selected from rheumatoid arthritis/seronegativearthropathies, osteoarthritis, inflammatory bowel disease, systematic lupus erythematosis, and iridocyclitis/uveitis/optic neuritis.

12. The method according to claim 10, wherein said cancerous disorder or cancerous condition is at least one selected from leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, and multiple myeloma.

13. The method according to claim 10 wherein said effective amount is 0.01-100 mg/kilogram of said cells, tissue, organ or animal for treating said immune condition, immune disorder or immune disease, or 0.0001-50 mg/kilogram of said cells, tissue, organ or animal for treating said cancerous disorder or cancerous condition.

14. The method according to claim 10, wherein said contacting or administering is by at least one mode selected from intravenous, intramuscular, bolus, subcutaneous, respiratory, inhalation, vaginal, rectal, buccal, sublingual, intranasal or transdermal.

15. A medical device, comprising at least one antibody or antibody fragment according to claim 1, wherein said device further comprising means for contacting or administering said at least one antibody or antibody fragment by at least one mode selected from intravenous, intramuscular, bolus, subcutaneous, respiratory, inhalation, vaginal, rectal, buccal, sublingual, intranasal, or transdermal.

16. A formulation comprising at least one antibody or antibody fragment according to claim 1, and at least one carrier selected from sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, and mixtures thereof, in an aqueous diluent.

17. The formulation according to claim 16, wherein the concentration of the antibody or antibody fragment in the formulation is from about 0.1 mg/ml to about 100 mg/ml.

18. A kit comprising at least one antibody or antibody fragment according to claim 1 in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate, thimerosal, and mixtures thereof in an aqueous diluent.

19. The kit according to claim 18, wherein reconstituting contents of the first and second containers produces a solution with a concentration of said antibody or antibody fragment of from about 0.1 mg/ml to about 500 mg/ml.

20. A method of inhibiting binding or specific activity of CD22 in a patient having a B cell cancer or a B cell dependent autoimmune disease, comprising administering to the patient with the formulation according to claim 16.

21. An article of manufacture for human pharmaceutical use, comprising packaging material and a container comprising a solution or a lyophilized form of at least one antibody or antibody fragment according to claim 1.

22. The article of manufacture according to claim 21, wherein said container is a glass or plastic container having a stopper for multi-use administration.

* * * * *